(12) United States Patent
Fabiani et al.

(10) Patent No.: US 9,164,048 B2
(45) Date of Patent: Oct. 20, 2015

(54) METHOD AND DEVICE FOR IDENTIFYING A MATERIAL OF AN OBJECT

(75) Inventors: Elisa Fabiani, La Buisse (FR); Jean Rinkel, Grenoble (FR); Joachim Tabary, Grenoble (FR); Jean-Marc Dinten, Lyons (FR)

(73) Assignee: Commissariat a l'energie atomique et aux energies alternatives, Paris (FR)

(*) Notice: Subject to any disclaimer, the term of this patent is extended or adjusted under 35 U.S.C. 154(b) by 787 days.

(21) Appl. No.: 13/383,531

(22) PCT Filed: Jul. 19, 2010

(86) PCT No.: PCT/EP2010/060414
§ 371 (c)(1),
(2), (4) Date: Jan. 11, 2012

(87) PCT Pub. No.: WO2011/009833
PCT Pub. Date: Jan. 27, 2011

(65) Prior Publication Data
US 2012/0123697 A1    May 17, 2012

(30) Foreign Application Priority Data

Jul. 20, 2009 (FR) ..................... 09 55011

(51) Int. Cl.
*G01N 23/203* (2006.01)
*G01V 5/00* (2006.01)
*G01N 37/00* (2006.01)

(52) U.S. Cl.
CPC ............ *G01N 23/203* (2013.01); *G01V 5/0025* (2013.01); *G01N 2223/615* (2013.01)

(58) Field of Classification Search
CPC .......... G01N 23/203; G01N 2223/615; G01V 5/0025
USPC ............... 702/22, 23, 28, 137; 378/57, 86–89
See application file for complete search history.

(56) References Cited

U.S. PATENT DOCUMENTS 3,243,589 A * 3/1966 Sinclair ........................ 378/86
4,817,122 A   3/1989 Badono et al.
(Continued)

FOREIGN PATENT DOCUMENTS

JP        61-193057      8/1986
WO   WO 2007/036359 A1   4/2007

OTHER PUBLICATIONS

French Preliminary Search Report issued Mar. 31, 2010 in Patent Application No. FR 0955011 with English Translation of Category of Cited Documents.

(Continued)

*Primary Examiner* — Alexander Satanovsky
(74) *Attorney, Agent, or Firm* — Oblon, McClelland, Maier & Neustadt, L.L.P.

(57) ABSTRACT

The invention relates to a device for identifying a material of an object having a source of X-Ray photons and a spectrometric detector, the source irradiating the object with an incident beam and the detector measuring a magnitude of a backscattered beam from the incident beam after scattering in a volume ($\delta V$) of the material and an energy of the X-Ray photons of the backscattered beam. The incident and backscattered beams forming a scattering angle ($\theta$). An adjusting device adjusts the position between the source, the detector and the object in order for the volume to be at different depths with a constant angle. A processing device processes the two magnitudes in two positions and the energy in one position and calculates an attenuation coefficient ($\mu$material ($E_0$, $E_1$, $\epsilon$)). An estimating device estimates the density ($\rho$) of the material.

13 Claims, 8 Drawing Sheets

(56) References Cited

U.S. PATENT DOCUMENTS

| | | | | |
|---|---|---|---|---|
| 5,600,700 A * | 2/1997 | Krug et al. | | 378/57 |
| 2005/0163282 A1 | 7/2005 | Zerle | | |
| 2007/0161885 A1* | 7/2007 | Kimchy | | 600/407 |
| 2008/0253525 A1 | 10/2008 | Boyden et al. | | |
| 2008/0285714 A1 | 11/2008 | Klein | | |
| 2009/0086906 A1* | 4/2009 | Clayton | | 378/57 |

OTHER PUBLICATIONS

Shiro Tuzi et al., "Locating the Positions of Reinforcing Bars in Reinforced Concrete Using Backscattered Gamma Rays", International Journal of Radiation Applications and Instrumentation: Part A. Applied Radiation and Isotopes, vol. 41, No. 10/11, XP000172902, Jan. 1, 1990, pp. 1013-1018.

Robert C. Runkle et al., "Photon and Neutron Interrogation Tehniques for Chemical Explosives Detection in Air Cargo: A Critical Review", Nuclear Instruments & Methods in Physics Research, Section-A : Accelerators, Spectrometers, Detectors and Associated Equipment, vol. 603, No. 3, XP026097560, May 21, 2009, pp. 510-528.

J. H. Hubbell et al., Errata, Erratum: Atomic Form Factors, Incoherent Scattering Functions, and Photon Scattering Cross Sections, J. Phys. Chem. Ref. Data, vol. 6, No. 2, 1977, pp. 615-616.

J. H. Hubbell et al., Atomic Form Factors, Incoherent Scattering Functions, and Photon Scattering Cross Sections, J. Phys. Chem. Ref. Data, vol. 4, No. 3, 1975, pp. 471-538.

U.S. Appl. No. 14/352,910, filed Apr. 18, 2014, Paulus, et al.

Office Action issued Oct. 17, 2014 in European Patent Application No. 10 733 003.7.

* cited by examiner

METHOD AND DEVICE FOR IDENTIFYING A MATERIAL OF AN OBJECT

TECHNICAL FIELD

The present invention relates to a method and a device for identifying a material of an object.

The detection of illicit substances in luggage constitutes an important security factor in everyday life. The aim of combating terrorism is to prevent explosives or hazardous chemicals placed in luggage to be loaded on board airplanes or to be hidden in packages left in public places such as railway stations, the underground, or airports. Drugs or smuggled cigarettes are also searched for by customs officers at both airports and borders.

STATE OF THE PRIOR ART

Devices for identifying the chemical composition of materials of an object developed until now exploit the absorption of the X radiation transmitted through the object to be inspected. However, in certain cases of voluminous objects or packages left against a wall, such devices operating by transmission are not suitable, because it is necessary to place the object to be inspected between the source of X-Ray photons and the detector detecting the transmitted X-Ray photons.

Other devices are based on backscattering. This technology only requires access to one side of the suspect object to be inspected. In this case, the source of X-Ray photons and the detector are located on the same side of the object. The X-Ray photons are going to bounce off the object more than pass through it.

This technique becomes a good inspection tool for the detection and the identification of explosives, which are materials in which the atoms constituting them have low atomic numbers, for example less than 10. Indeed, they are constituted of carbon, oxygen, hydrogen, nitrogen. In this case, the phenomenon of Compton effect scattering is preponderant compared to the phenomenon of absorption by photoelectric effect at the energies conventionally used, comprised between around 50 and 200 keV.

A device for identifying a material of an object commercialised by the American Science and Engineering Inc company using "Z® Backscatter" technology and "Flying Spot" technology will now be described. Other similar devices have been developed by the Rapiscan or PCO Inc companies.

Reference is made to FIG. 1. A polychromatic source of X-Ray photons 1 supplies a long and thin beam of X-Ray photons 2 towards an object to be inspected 3. The beam of X-Ray photons is composed of photons of different energies. It is assumed that the object to be inspected 3 is a luggage containing blocks of plastic explosive. A detector of X-Ray photons 4 has been represented downstream of the object to be inspected 3 and a pair 5 of detectors of X-Ray photons upstream of the object to be inspected 3 on either side of the beam of X-Ray photons 2.

Some X-Ray photons will thus be transmitted by the atoms of the object to be inspected 3 and detected by the detector of X-Ray photons 4 downstream and others will be backscattered by the atoms of the object to be inspected 3 and detected by the pair of upstream detectors of X-Ray photons 5.

The beam of X-Ray photons 2 is providing with a movement of scanning the object to be inspected 3 so that the position of the beam of X-Ray photons 3 is defined at each instant and that each measurement of the signal detected by a detector is correlated with a particular region of the object to be inspected 3. The interpretation of results is easy and rapid.

In addition, thanks to the long and thin scanning beam of X-Ray photons, the radiation doses may be much lower than in conventional inspection devices with a fan shaped beam of X-Ray photons.

It should be noted that the American Science and Engineering company commercialises under the registered trade name "Z®Backscatter Van™" a system of inspection by backscattering alone, integrated in a lorry which enables the inspection of moving vehicles and cargos, the system being stationary.

The drawback of the device that has just been described is that detectors of X-Ray photons operate in charge integration mode. The X-Ray photons that reach the detector are converted into electric charges and the electric charges created in a given pixel of the detector are integrated during an exposure time. During this exposure time, the total energy of the X-Ray photons is known and it is possible to access unique information which is the mean attenuation of the inspected material corresponding to the given pixel over the different energies of the irradiation spectrum since the beam of X-Ray photons is polychromatic. This mean attenuation is due to the density p of the inspected material. But the integrated signal does not enable two materials having the same mean attenuation to be distinguished. To do so, it would be necessary to have available additional information, which is the atomic number Z of the inspected material. This additional information is difficult to access with the integrated signal.

The device for identifying a material thus induces numerous false alarms since the chemical composition of explosives is similar to that of a large number of everyday materials which can exhibit the same characteristics in terms of density $\rho$.

DESCRIPTION OF THE INVENTION

The aim of the present invention is to propose a method for identifying a material of which an object is composed, said material being buried or on the surface of the object, as well as a device for identifying the material, said method and said device not having the above limitations and difficulties.

An aim of the invention is to propose a reliable method for identifying illicit liquid or solid substances contained in luggage to improve security in airports. This identification can take place whatever the nature of the luggage and the position of the substance in the luggage.

Another aim of the invention is to propose a method that makes it possible to easily distinguish water compared to an explosive liquid.

To achieve this, the present invention proposes exploiting the spectral signature backscattered by an object, irradiated by a beam of incident X-Ray photons, said spectral signature being delivered by a spectrometric detector. The method that is the subject matter of the invention proposes at least two irradiations of the object positioned at two different distances with respect to the source of X-Ray photons-spectrometric detector assembly.

More specifically, the present invention proposes a method for identifying a material of an object, said material being provided with a rank i (i whole number), i being equal to one if it is at the surface and being greater than one if it is buried under i−1 layers, in which:

a°) a substantially flat surface, at least locally, of the object is irradiated with a beam of incident X-Ray photons generated by a collimated source of X-RAY photons, b°) using a collimated spectrometric detector, a first flux of a beam of backscattered X-Ray photons generated after scattering is measured, along a given angle θ of scattering, of the beam of incident X-Ray photons in a first inspection volume of the material of rank i located at a first depth in the material of rank i, c°) using the collimated spectrometric detector, a second flux of a beam of backscattered X-Ray photons generated after scattering is measured along the same given angle θ of scattering, of the beam of incident X-Ray photons in a second inspection volume of the material of rank i located at a second depth in the material of rank i, d°) using the measurements of the two fluxes of X-Ray photons (Xi1($E_1$), Xi2($E_1$)) a combined attenuation coefficient $\mu'_{material.i}$ ($E_0,E_1\epsilon$) is calculated in which $E_0$ is the energy of the X-Ray photons of the beam of incident X-Ray photons and $E_1$ the energy of the X-Ray photons of the beam of backscattered X-Ray photons along the given scattering angle and $\epsilon = li'1/li1 = li'2/li2$, li1 respectively li2 being the distance traveled by the beam of incident X-Ray photons in the material of rank i up to the first respectively second inspection volume, li'1 respectively li'2 being the distance traveled by the beam of backscattered X-Ray photons in the material of rank i from the first, respectively, second inspection volume, the combined attenuation coefficient comprising a natural logarithm of a ratio between the two fluxes Xi1 ($E_1$), Xi2($E_1$);

e°) a mean of the combined attenuation coefficient $\mu'_{material.i}$ ($E_0,E_1,\epsilon$) over a given energy range of X-Ray photons of the beam of backscattered X-Ray photons is defined;

f°) the density of the material of rank i is estimated from the mean of the combined attenuation coefficient.

The combined attenuation coefficient preferably meets the formula:

$$\mu'_{matériau.i}(E_0, E_1, \varepsilon) = -\frac{1}{li1 - li2} \ln\left(\frac{Xi1(E_1)}{Xi2(E_1)}\right)$$

To identify more precisely the material of rank i and determine its chemical nature, it is possible to calculate a parameter $\beta(E_1, Material.i, \theta)$ describing the phenomenon of scattering in the material of rank i using measurements of the two fluxes of X-Ray photons (Xi1 ($E_1$), Xi2($E_1$)). This parameter is expressed by:

$$\beta(E_1, Matériau \cdot i, \theta) = \frac{Xi2(E_1)^{\frac{li1}{li1-li2}}}{Xi1(E_1)^{\frac{li2}{li1-li2}}}.$$

This parameter $\beta(E_1 \text{Material.i}, \theta)$, the combined attenuation coefficient $\mu'_{material.i}$ ($E_0,E_1,\epsilon$) and the density of the material of rank i may be used.

The ratio $\beta(E_1, Material.i, \theta)/(k(E_0\theta)\rho$ is then used as a function of the density, $k(E_0,\theta)$ being a parameter independent of the material of rank i but dependent on the energy of the beam of incident X-Ray photons, the scattering angle, and the position of the source of X-Ray photons and the spectrometric detector with respect to the inspected volume, this ratio being substantially equal to the ratio of the effective atomic number $Z_{eff}$ of the material over its normalised molar mass $A_{norm}$.

The distances li1, li2, li'1, li'2 may be calculated from the relative positions of the source of X-Ray photons, the spectrometric detector and the object and if i is different from 1, a distance lj traveled by the beam of incident X-Ray photons in each of the one or more materials of rank 1 to i−1, and a distance l'j traveled by the beam of backscattered X-Ray photons along the angle θ in each of the one or more materials of rank 1 to i−1 while:

1°) making successive measurements of the flux of beams of backscattered X-Ray photons for inspection volumes situated at greater and greater depths, from the surface layer and spaced apart by a step (p), the scattering angle remaining substantially constant from one measurement to the next, 2°) calculating for a first, a second and a third flux $X_1(E_1)$, $X_2(E_1)$ and $X_3(E_1)$ of beams of backscattered X-Ray photons a first combined attenuation coefficient $$\mu'_1(E_0, E_1, \varepsilon) = -\frac{1}{lj1 - lj2} \ln\left(\frac{X_1(E_1)}{X_2(E_1)}\right)$$

and a second combined attenuation coefficient $$\mu'_2(E_0, E_1, \varepsilon) = -\frac{1}{lj2 - lj3} \ln\left(\frac{X_2(E_1)}{X_3(E_1)}\right),$$

with $\epsilon = l'j1/l'j1 = l'j2/lj2 = l'j3/lj3$, lj1, lj2, lj3 and respectively l'j1, l'j2, l'j3 being distances traveled by the beam of incident X-Ray photons and respectively the beam of backscattered X-Ray photons, in the material in which is located the inspection volume for which the measurement is carried out, these distances being calculated from the relative position between the source of X-Ray photons, the spectrometric detector and the object.

3°) comparing the first and the second combined attenuation coefficient,

4°) as soon as a difference appears, the searched for distance lj is the greater of the distances used in the formula of the first combined attenuation coefficient, 5°) by reiterating steps 2°) to 4°) one or more times while taking three successive measurements of the flux of beams of backscattered X-Ray photons, two of which are successive measurements used for the preceding calculation of step 2°), the calculation of the distances traveled by the beam of X-Ray photons in the material in which is located the inspection volume for which the measurement is carried out taking into account the distances lj and l'j determined previously.

The attenuation factor Fi may be expressed by $$Fi = \prod_{j=1}^{i-1} e^{-\mu'_{matériau.i}(E_0, E_1, \varepsilon)lj},$$

$\epsilon$ equaling l'j/lj and $\mu'_{material.j}$ ($E_0,E_1,\epsilon$) being a combined attenuation coefficient in the material of rank j, this combined attenuation coefficient being calculated from two measurements of the flux of X-Ray photons of beams of backscattered X-Ray photons for two inspection volumes situated at two different depths in the material of rank j, the scattering angle remaining substantially constant, lj respectively l'j being distances traveled by the beam of incident respectively backscattered X-Ray photons in the material of rank j respectively before and after the scattering.

The parameter independent of the material $k(E_0,\theta)$ is expressed by $$k(E_0, \theta) = C(E_0, \theta) \cdot F(E_0) \left[ \frac{d\sigma_{Kn}(E_0, \theta)}{d\Omega} \delta\omega N_a \cdot \partial V \right]$$

with $F(E_0)$ the flux density at the energy $E_0$ of the beam of incident X-Ray photons, $N_a$ Avogadro's number, $$\frac{d\sigma_{KN}(E_0, \theta)}{d\Omega}$$

the differential cross section of scattering per electron by Compton effect approximated by a formula called Klein-Nishina, $\delta\omega$ the solid angle under which is seen the spectrometric detector from each point of the inspection volume $\delta V$, $C(E_0,\theta)$ the efficiency of the spectrometric detector at the energy $E_1$ which is the energy of the beam of backscattered X-Ray photons, this beam of X-Ray photons having the energy $E_0$ before scattering, along the given scattering angle $\theta$.

The parameter $k(E_0,\theta)$ may be obtained by modelling or by measurements in a standard material.

The present invention also relates to a device for identifying a material of an object comprising a source of X-Ray photons-collimated spectrometric detector assembly, the source of X-Ray photons being intended to irradiate a substantially flat surface, at least locally, of the object with a beam of incident X-Ray photons, the X-Ray photons of which have an energy $E_0$, the spectrometric detector being intended to measure a flux of a beam of backscattered X-Ray photons generated after scattering of the beam of incident X-Ray photons in an inspection volume of the material, the X-Ray photons of the beam of X-Ray photons having an energy $E_1$, the beam of incident X-Ray photons and the beam of backscattered X-Ray photons forming a scattering angle, the vertex of which is the inspection volume. It moreover comprises:
 a means for adjusting the relative position between the source of X-Ray photons, the spectrometric detector and the object so as to place the inspection volume in at least two positions at different depths in the material while maintaining a substantially constant scattering angle,
 means for processing two fluxes of beams of backscattered X-Ray photons measured by the spectrometric detector in at least two positions and calculating a combined attenuation coefficient $\mu'_{material}(E_0,E_1,\epsilon)$ using these two fluxes of measured beams of backscattered X-Ray photons,
 means for estimating the density of the material from the combined attenuation coefficient averaged over a given range of energy of the X-Ray photons of the beam of backscattered X-Ray photons.

The processing and calculation means can enable a parameter $\beta(E_1,\text{Material}.i,\theta)$ describing the phenomenon of scattering in the material of rank i to be calculated.

The device for identifying a material may also comprise means for determining the chemical nature of the material using the parameter $\beta(E_1,\text{Material}.i,\theta)$, the combined attenuation coefficient $\mu'_{material}(E_0, E_1,\epsilon)$ and the density.

The determination means may use the value of the ratio $\beta(E_1,\text{Material}.i,\theta)/(k(E_0,\theta)\rho$ as a function of the density, the ratio expressing the chemical nature of the material, $k(E_0,\theta)$ being a parameter independent of the material but dependent on the energy of the beam of incident X-Ray photons, the scattering angle, and the position of the source of X-Ray photons and the spectrometric detector with respect to the inspected volume.

With a view to simplification, it is preferable that the beam of incident X-Ray photons forms an angle with an irradiated surface of the object which is substantially equal to the angle that the beam of backscattered X-Ray photons makes with the irradiated surface of the object.

Preferably a same scattering angle over two successive measurements is maintained.

The means of adjusting can bring together and/or move apart the source of X-Ray photons-spectrometric detector assembly with respect to the object and bring together and/or move apart the source of X-Ray photons of the spectrometric detector.

The means of adjusting can operate step by step, while bringing together and/or the moving apart the source of X-Ray photons-spectrometric detector assembly with respect to the object, the step being smaller than the thickness of a layer of material of the object so that the inspection volume can take at least two positions in the layer of material.

BRIEF DESCRIPTION OF DRAWINGS

The present invention will be better understood on reading the description of embodiment examples given for purely illustrative purposes and in no way limiting, and by referring to the appended drawings in which.

Identical, similar or equivalent parts of the different figures described hereafter bear the same numerical references so as to make it easier to go from one figure to the next.

The different parts in the figures are not necessary represented at a uniform scale, in order to make the figures more legible.

Detailed Description of Specific Embodiments

It will now be explained, in the case of a material formed of a single chemical element, how to identify it. This chemical element is characterised by its atomic number Z, in other words its number of atoms, and by its density $\rho$.

When an X photon enters into collision with a free electron or one weakly bonded to the material, it transfers to it part of its energy hv. A photon of lower energy is then diffused in a different direction from the incident direction, the two directions are separated by an angle $\theta$ called scattering angle and the electron is ejected from its position. The quantity of energy of the resulting photon hv' is governed by the Compton equation.

The quantity of Compton diffused radiation, for a given energy of the incident X photon and a given scattering angle $\theta$, is proportional to what is called the incoherent scattering function S(x,Z), which corresponds to the number of electrons per atom that can induce Compton scattering.

In the incoherent scattering function, the parameter x, called transfer of the quantity of movement and expressed in $cm^{-1}$ is defined by the expression:

$$x = \frac{1}{\lambda_0}\sin(\theta/2) = \frac{E_0}{hc}\sin(\theta/2) \approx \frac{E_0}{12,399}\sin(\theta/2) \quad (1)$$

$E_0$ represents the energy of the incident X photon in keV. The atomic differential cross section by Compton scattering, which is the majority at energies greater than around 10 keV, is given by the product of S(x,Z) by the differential cross section of scattering per electron by Compton effect $$\frac{d\sigma_{KN}(E_0,\theta)}{d\Omega},$$

given by the Klein-Nishina formula.

In the case of a material which is not a simple body, but which is a mixture comprising n chemical elements, it is possible to generalise and to define the incoherent scattering function in the following manner:

$$S(x,Z) = \sum_{i=1}^{n} \alpha_i^{at} S(x,Z_i) \quad (1')$$

with $\alpha_i^{at}$ the percentages in atoms of each element and $S(x, Z_i)$ the incoherent scattering function for each element, these functions have been tabulated by Hubbell et al. in "Atomic form factors, incoherent scattering functions, and photon scattering cross sections", J.: Phys. Chem. Ref. Data 4, (1975), pages 71-538; erratum (1977), 6, pages 615-616.

Each $\alpha_i^{at}$ is defined from the percentage by mass $\omega_i$ and the atomic mass $A_i$ of the chemical element $$i: \alpha_i^{at} = \frac{\frac{\omega_i}{A_i}}{\sum_{i=1}^{n}\frac{\omega_i}{A_i}}. \quad (2)$$

Figure 1:
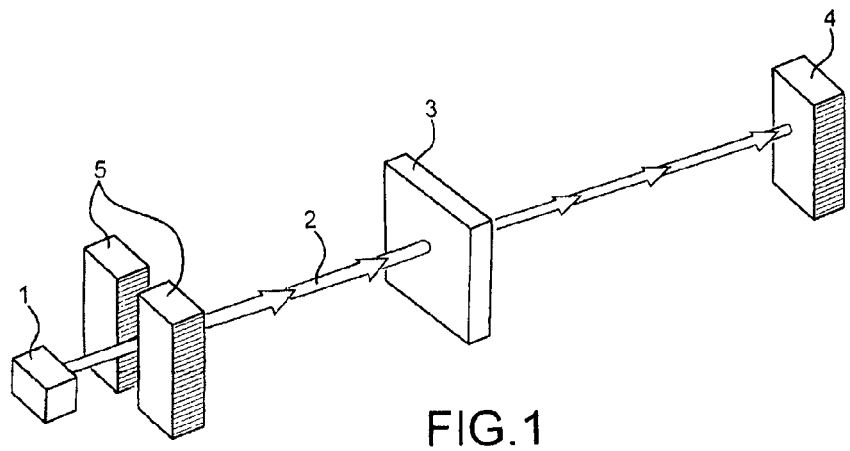
FIG. 1, already described, shows a device for identifying a material of an object of the prior art.
Figure 2:
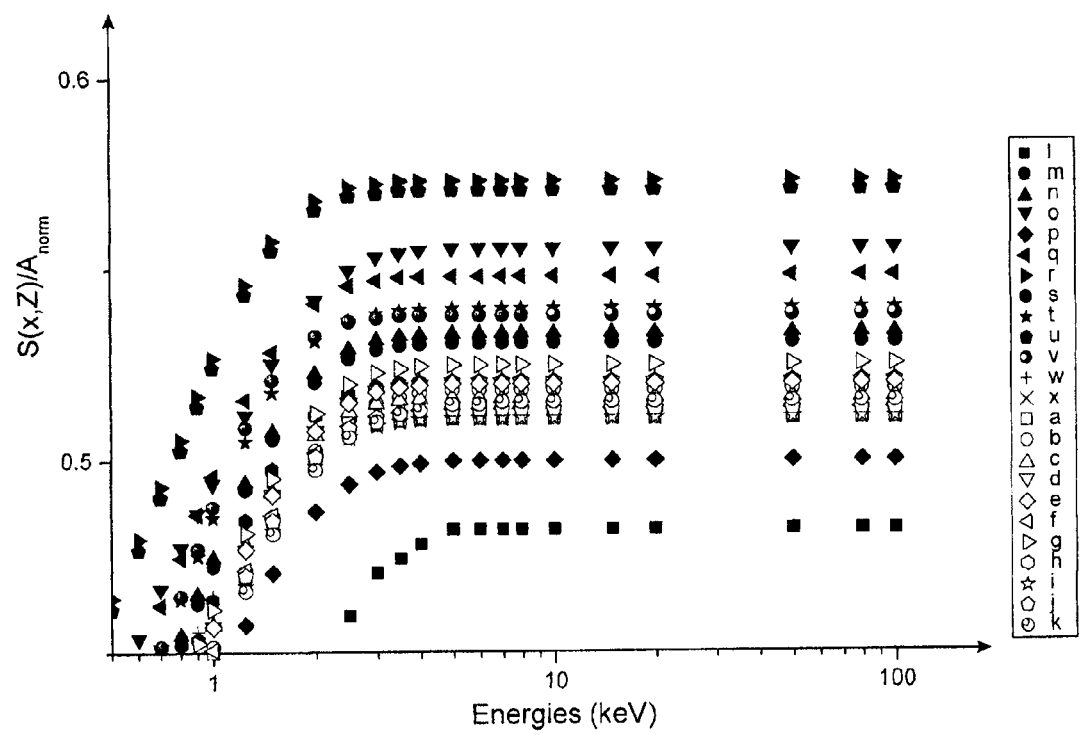
FIG. 2 is a graph representing the incoherent scattering function $S(x, Z)$, for a scattering angle of 120°, as a function of the energy of the X-Ray photons detected for a series of 24 materials of interest, explosive or not.

For a given scattering angle $\theta$, above a certain energy, it will be noticed that the function S(x,Z) tends towards an asymptote. In the example of FIG. 2, for a scattering angle $\theta$ of 120°, it may be seen that this asymptote is obtained for energies above around 10 keV. A parameter of the same nature as the atomic number Z, but noted $Z_{eff}$ and called effective atomic number, is thus defined. It characterises the mixture and corresponds to the asymptote of the function S(x,Z). The inventors have thus established that the function S(x, Z) tends towards $Z_{eff}$. In a similar manner, a normalised molar mass $A_{norm}$ is defined by:

$$A_{norm} = \sum_i \alpha_i^{at} A_i.$$

If the magnitude $S(x,Z)/A_{norm}$ is represented as a function of energy as illustrated in FIG. 2, it will be noted that the curves representative of different explosives such as TNT (trinitrotoluene) (a), ammonal composed of ammonium nitrate, aluminium powder and Tolite)(b), DNT (dinitrotoluene)(c), gum dynamite (d), $C_{105}H_{417}N_{200}O_{374}$ (commercialised under the name of Gelamon 22 by Sprengstoffwerke Gnaschwittz GmbH) (e), Hexogen (cyclotrimethylene trinitramine) (f), ammonium nitrate (g), nitroglycol (h), nitroglycerine (i), nitropentrite (j), black blasting powder (k) are easily distinguishable from the curves of the different materials conventionally encountered in luggage such as aluminium (l), cellulose (m), Delrin (n) which is a polyoxymethylene (or polyformaldehyde) commercialised by Du Pont, water (o), Kynar (p) which is a PVDF (polyvinylidene fluoride) commercialised by Arkema, nylon (q), paraffin (r), PEPT (s), Plexiglas (t), polyethylene (u), polystyrene (v), polyvinyl (w), Teflon (x) which is a polytetrafluoroethylene (PTFE) commercialised by Du Pont.

The curves of FIG. 2 have been drawn using the formula (1') from data tabulated by Hubbell. The magnitude $S(x,Z)/A_{norm}$ thus bears information reflecting the chemical nature of the material studied.

Figure 3:
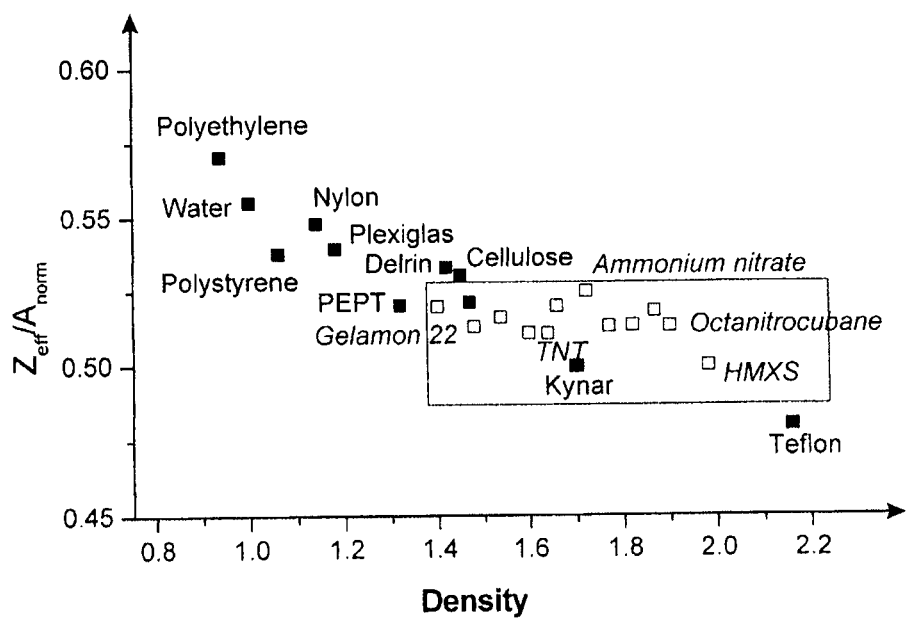
FIG. 3 is a representation of the ratio of the effective atomic number over the normalised molar mass as a function of density for twenty or so materials of interest, said representation making it possible to identify the material, said representation being exploited by the method of the invention.

By representing the space $Z_{eff}/A_{norm}(\rho)$ as in FIG. 3, a zone is defined characteristic of explosives for densities above 1.4 and a magnitude $Z_{eff}/A_{norm}$ comprised between around 0.48 and 0.53. This zone is boxed.

The method for identifying a material that is the subject matter of the invention makes it possible to estimate the density $\rho$ and moreover optionally the magnitude $Z_{eff}/A_{norm}$ which makes it possible to determine the chemical nature of the searched for material.

To do this, a source of X-Ray photons is going to be used, intended to produce a beam of X-Ray photons and a spectrometric detector and carry out multi-depth measurements.

Figure 4:
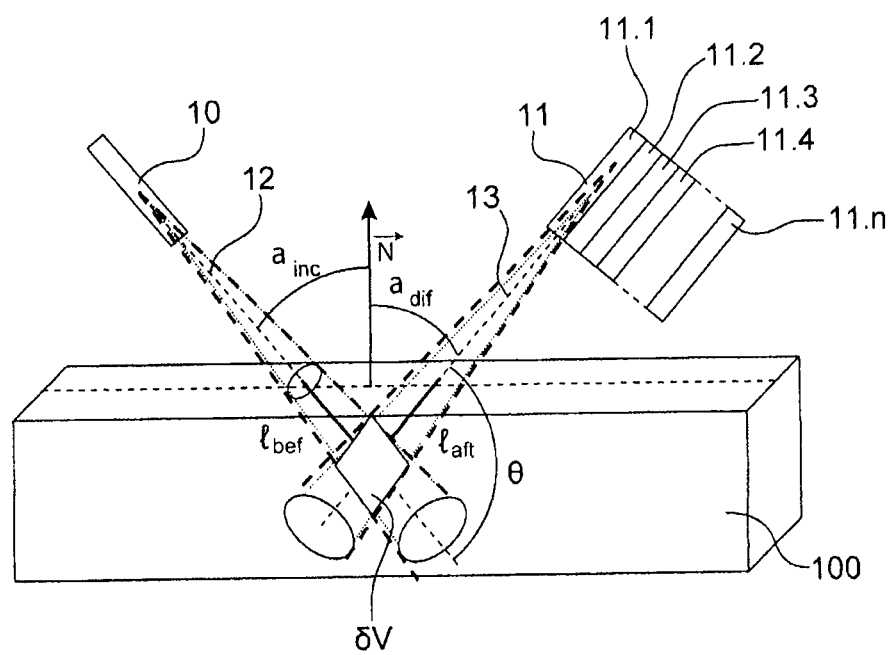
FIG. 4 represents a beam of incident X-Ray photons irradiating a material, a beam of backscattered X-Ray photons from the beam of incident X-Ray photons having diffused in an inspection volume of the material.

Reference is made to FIG. 4, which shows a device making it possible to implement the method of the invention. The source of X-Ray photons bears the reference 10, the spectrometric detector bears the reference 11. It is assumed that in the example described, the object 100 is composed of a homogeneous material and comes in the form of a substantially rectangular block of known thickness. It will be seen later that the method of the invention may also be employed if the object 100 comprises several materials in layers stacked at least locally. It suffices that the object has a substantially flat surface, at least locally, said surface having to be irradiated by the X-Ray photons emitted by the source.

The source of X-Ray photons 10 and the spectrometric detector 11 are collimated, the angle of collimation is generally small, preferentially less than around 10° and more particularly less than 5°. The source of X-Ray photons 10 may be monochromatic, for example an isotopic source, or instead polychromatic, for example an X ray generating tube. Since the intensity of the radiations produced by X ray generating tubes are greater than that of the radiations produced by isotopic sources, X ray generating tubes are preferred.

The source of X-Ray photons 10 is intended to produce a beam of incident X-Ray photons 12, the spectrum of which is a function of the energy $E_0$. The beam of incident X-Ray photons 12 penetrates into the material of the object 100, at the level of a substantially flat zone, and diffuse into an inspection volume $\delta V$, situated at a given depth. An attenuation takes place between the emission by the source of X-Ray photons 10 and the inspection volume $\delta V$. A beam of backscattered X-Ray photons 13 is generated and it is captured by the spectrometric detector 11. An attenuation takes place between the inspection volume $\delta V$ and the spectrometric detector 11. The inspection volume $\delta V$ corresponds to the intersection between the beam of incident X-Ray photons 12 and the beam of backscattered X-Ray photons 13 towards the spectrometric detector 11. Due to the collimation of the source of X-Ray photons 10 and the spectrometric detector 11, the beams of incident and backscattered X-Ray photons are delimited spatially, which makes it possible to define a relatively small inspection volume $\delta V$, typically of the order of a centimeter cube. The angles of collimation of the source of X-Ray photons 10 and the spectrometric detector 11 will be chosen consequently. The beam of incident X-Ray photons 12 and the beam of backscattered X-Ray photons 13 are separated by a scattering angle $\theta$, as illustrated in FIG. 4.

The vertex of the scattering angle $\theta$ is the intersection between the central axis of the beam of incident X-Ray photons 12 and the beam of backscattered X-Ray photons 13 towards the spectrometric detector 11. These central axes are represented in dotted lines in FIG. 4. The scattering angle $\theta$ is equal to 0° when the two central axes are in the extension of each other.

As will be seen later, at least two consecutive measurements are made of a magnitude relative to the radiation of the beam of backscattered X-Ray photons 13 towards the spectrometric detector 11. To do this, one moves the source of X-Ray photons 10, the spectrometric detector 11 and the object 100 relatively with respect to each other so that the scattering takes place at different depths in the material. The two positions are only illustrated in FIG. 5 described later. The movement of the source of X-Ray photons 10 and the spectrometric detector 11 between the two consecutive measurements will be carried out while maintaining the same scattering angle 8. This movement could for example take place in a direction substantially perpendicular to the surface of the examined object, this surface being assumed substantially flat, at least locally.

The beam of incident X-Ray photons 12 forms an angle $\alpha_{inc}$ with a normal N to the irradiated surface of the object 100. The beam of backscattered X-Ray photons 13 forms an angle $\alpha_{dif}$ with the normal N to the irradiated surface of the object 100. The angles $\alpha_{inc}$ and $\alpha_{dif}$ are not necessarily equal, on the other hand, preferentially, the angles $\alpha_{inc}$ and $\alpha_{dif}$ remain substantially constant during two consecutive measurements.

Let us now consider the flux density of the beam of incident X-Ray photons. This flux density is noted $F(E_0)$. This flux density $F(E_0)$ is one of the characteristics of the source of X-Ray photons 10. It will be recalled that the fluence is the quotient of a number of X-Ray photons emitted or detected per unit of surface and the flux density, the fluence per unit of time. $X(E1)$ designates the flux of X-Ray photons of the beam of backscattered X-Ray photons 13 along the scattering angle $\theta$ towards the spectrometric detector 11, this flux of X-Ray photons being measured by the spectrometric detector 11. It will be recalled that the flux corresponds to the number of X-Ray photons emitted or detected per unit of time.

This flux $X(E_1)$ is expressed by:

$$X(E_1) = C(E_0, \theta) \cdot F(E_0) \cdot e^{-\mu_{materiau}(E_0, Z) \cdot l_{bef}} \quad (3)$$

$$\left[ \frac{d\sigma_{Kn}(E_0, \theta)}{d\Omega} \delta\omega \frac{N_a \cdot S(x, Z) \cdot \rho}{A_{norm}} \cdot \delta V \right] e^{-\mu_{materiau}(E_1) \cdot l_{aft}}$$

where:

$$E_1 = \frac{E_0}{1 + \alpha(1 - \cos\theta)}$$

is the energy of the X-Ray photons detected by the spectrometric detector after the scattering along the scattering angle $\theta$ and $\alpha = E_0/m_e c^2$, $m_e$ is the mass of the electron at rest, i.e. $9.1093097 \times 10^{-31}$ kg and c the speed of light in a vacuum, i.e. 299792458 m/s, the X-Ray photons of the beam of incident X-Ray photons before scattering having the energy $E_0$;

$C(E_0, \theta)$ is an efficiency coefficient, equal to the ratio between the flux of X-Ray photons measured by the spectrometric detector at the energy $E_1$ over the flux of X-Ray photons of the beam of backscattered X-Ray photons arriving at the spectrometric detector at the same energy $E_1$, the energy $E_1$ depending on the energy $E_0$ as has just been seen in the previous paragraph;

$\mu_{material}(E_0)$ and $\mu_{material}(E_1)$ are linear attenuation coefficients of the material before and after scattering at the respective energies $E_0$ and $E_1$;

$l_{bef}$ is the distance traveled by the beam of incident X-Ray photons in the material before scattering;

$l_{aft}$ is the distance traveled by the beam of backscattered X-Ray photons in the material after scattering;

$$\frac{d\sigma_{KN}(E_0, \theta)}{d\Omega}$$

is the differential cross section of scattering per electron by Compton effect given by the Klein-Nishina formula;

$\delta\omega$ is the solid angle under which the spectrometric detector is seen from each point of the inspection volume $\delta V$, said solid angle is not illustrated so as not to clutter FIG. 4;

$N_a$ is Avogadro's number;

$S(x,Z)$ is the incoherent Compton scattering function, it tends towards $Z_{eff}$ as has been seen previously.

The other parameters have already been presented.

In formula (3), three parameters depend on the material to be identified, namely:

ρ the density of the material, which is the term that most differentiates two different materials.

σ(E), which is the mass attenuation coefficient of the material, it is generally expressed in cm²/g, this parameter is contained in the attenuation terms before and after scattering namely:

$e^{-\mu_{material}(E_0)1_{bef}} = e^{-\sigma(E_0)\rho 1_{bef}}$ and
$e^{-\mu_{material}(E_1)1_{aft}} = e^{-\sigma(E_1)\rho 1_{aft}}$ For the searched for materials based on carbon, oxygen, hydrogen, nitrogen, fluorine, etc., σ(E) exhibits a small variation with respect to that of the density ρ with which it is multiplied to express the linear attenuation coefficient μ(E). Thus, the linear attenuation coefficient μ(E) depends very considerably on the density of the material, as illustrated in FIG. 6B. Consequently, the mass attenuation coefficient of the material σ(E) only bears little information concerning the nature of the material that it is wished to identify.

S(x, Z) is the incoherent scattering function, which is linked to the number of electrons that scatter per atom of the chemical elements constituting the material to be identified.

Formula (3) is valid if the distances $l_{bef}$ and $l_{aft}$ respectively separating different points of the inspection volume δV of the source of X-Ray photons 10 respectively of the spectrometric detector 11 do not vary substantially. This signifies that the dimensions of the sides of the volume δV are small given the distances $l_{bef}$ and $l_{aft}$.

In formula (3), one notes $$k(E_0, \theta) = C(E_0, \theta) \cdot F(E_0)\left[\frac{d\sigma_{Kn}(E_0, \theta)}{d\Omega}\delta\omega N_a \cdot \delta V\right].$$

The parameter $k(E_0,\theta)$ does not depend on the material to be identified. This parameter may be calculated by simulation or obtained by measurement of a magnitude relative to the radiation of the beam of backscattered X-Ray photons towards the spectrometric detector, knowledge of the experimental characteristics δω, θ, δV defined by the positioning of the source of X-Ray photons 10—spectrometric detector 11 assembly with respect to the object 100 and use of the Klein-Nishina formula. It will be noted nevertheless that this parameter $k(E_0,\theta)$ is difficult to estimate with precision, especially when a non mono-energetic source of X-Ray photons is used. Thus, according to an embodiment of the invention, $k(E_0,\theta)$ is determined in an experimental manner using a known material called standard. Details of this method for obtaining the parameter $k(E_0,\theta)$ will be given later in the description.

One also notes:

$$\beta(E_1, Mat\acute{e}riau, \theta) = \frac{S(x,Z)\cdot\rho}{A_{norm}}k(E_0, \theta) \approx \frac{Z_{eff}\cdot\rho}{A_{norm}}k(E_0, \theta),$$

β$E_1$,Material,θ) is a parameter describing the phenomenon of scattering in the material. The near equality is only valid above a certain energy, particularly above several keV, as may be seen in FIG. 2.

It is the magnitude $$\frac{Z_{eff}\cdot\rho}{A_{norm}}$$

that the method according to the invention is going to make it possible to estimate.

$$X(E_1) = \beta(E_1, Mat\acute{e}riau, \theta)\cdot e^{-\mu'_{mat\acute{e}riau}(E_0)\cdot l_{bef}-\mu'_{mat\acute{e}riau}(E_1)\cdot l_{aft}} \quad (4)$$

$$= \beta(E_1, Mat\acute{e}riau, \theta)\cdot$$

$$e^{-\mu'_{mat\acute{e}riau}(E_0)\cdot l_{vef}\left[1+\frac{\mu'_{mat\acute{e}riau}(E_1)\cdot l_{aft}}{\mu'_{mat\acute{e}riau}(E_0)\cdot l_{bef}}\right]}$$

$$= \beta(E_1, Mat\acute{e}riau, \theta)\cdot$$

$$e^{-\mu'_{mat\acute{e}riau}(E_0)\cdot l_{bef}\left[1+\frac{\mu'_{mat\acute{e}riau}(E_1)}{\mu'_{mat\acute{e}riau}(E_0)}\varepsilon\right]}$$

$$= \beta(E_1, Mat\acute{e}riau, \theta)\cdot e^{-\mu'_{mat\acute{e}riau}(E_0,E_1,\varepsilon)\cdot l_{bef}}$$

with $$\mu'_{mat\acute{e}riau}(E_0, E_1, \varepsilon) = \mu'_{mat\acute{e}riau}(E_0)\cdot\left[1+\frac{\mu'_{mat\acute{e}riau}(E_1)}{\mu'_{mat\acute{e}riau}(E_0)}\varepsilon\right]$$

and $$\varepsilon = \frac{l_{aft}}{l_{bef}}\mu'_{mat\acute{e}riau}(E_0, E_1, \varepsilon)$$

is a coefficient known as combined attenuation coefficient of the material, because it is established according to a combination of the linear attenuation coefficient of the material at the energies $E_0$ and $E_1$.

Since it is assumed that the inspected object 100 has a substantially flat surface, at least locally, in other words at least at the level of the intersection of the object with the beam of incident X-Ray photons and the beam of backscattered X-Ray photons, the factor ε is constant for any inspection depth and the combined attenuation coefficient μ' is independent of the depth. This surface forms a boundary of the object 100 with an ambient environment.

To estimate the searched for magnitude $$\frac{Z_{eff}\cdot\rho}{A_{norm}},$$

it is thus necessary to know separately the parameter β($E_1$, Material,θ), the parameter $k(E_0,\theta)$ as well as the combined attenuation coefficient μ'$_{material}$ ($E_0$, $E_1$,ε). To do this, two successive measurements are thus made of the flux of X-Ray photons of backscattered beams detected by the spectrometric detector 12, each of the measurements being made at a specific inspection depth.

$X_1(E_1)$ designates the flux of X-Ray photons of the beam of backscattered X-Ray photons 13 detected by the spectrometric detector 11 whereas the source of X-Ray photons 10 and spectrometric detector 11 assembly is in a first inspection position P1 and $X_2(E_1)$ the flux of X-Ray photons of the beam of backscattered X-Ray photons 13 detected by the spectrometric detector 11 whereas the source of X-Ray photons 10 and spectrometric detector 11 assembly is in a second inspection position P2. For the first inspection position P1, the distance traveled by the beam of incident X-Ray photons 12 in the material up to the inspection volume δV is noted $l_1$ or lb$_{ef1}$ depending on the locations. For the second inspection position P2, the distance traveled by the beam of incident X-Ray photons 12 in the material up to the inspection volume $\delta V$ is noted $l_2$ or $l_{bef2}$ depending on the locations.

It is possible to place oneself in conditions such that $\epsilon = l_{afi1}/l_{bef1} = l_{afi2}/l_{bef2}$ and thus that $\epsilon = l_{afi1}/l_1 = l_{afi2}/l_2$. It suffices in particular to carry out the measurements of $X_1(E_1)$, $X_2(E_1)$ that $\alpha_{inc1} = \alpha_{inc2}$ and that $\alpha_{dif1} = \alpha_{dif2}$. If this is not the case, the system of equations is resolved by making the hypothesis that the two preceding ratios are equal. One then obtains:

$$X_1(E_1) = \beta(E_1, \text{Material}, \theta) \cdot e^{-\mu'_{material}(E_0, E_1, \epsilon) l_1} \quad (5)$$

$$X_2(E_1) = \beta(E_1, \text{Material}, \theta) \cdot e^{-\mu'_{material}(E_0, E_1, \epsilon) l_2} \quad (6)$$

The ratio is calculated between $X_1(E_1)$ and $X_2(E_1)$.

$$\frac{X_1(E_1)}{X_2(E_1)} = \frac{\beta(E_1, \text{Matériau}, \theta) \cdot e^{-\mu'_{matériau}(E_0, E_1, \varepsilon) l_1}}{\beta(E_1, \text{Matériau}, \theta) \cdot e^{-\mu'_{matériau}(E_0, E_1, \varepsilon) l_2}} \quad (7)$$

One sets $\Delta l = l_1 - l_2$ $$\ln\left(\frac{X_1(E_1)}{X_2(E_1)}\right) = \ln\left(e^{-\mu'_{matériau}(E_0, E_1, \varepsilon) \cdot \Delta l}\right) \quad (8)$$

$$\ln\left(\frac{X_1(E_1)}{X_2(E_1)}\right) = -\mu'_{matériau}(E_0, E_1, \varepsilon) \cdot \Delta l \quad (9)$$

$$\mu'_{matériau}(E_0, E_1, \varepsilon) = -\frac{1}{\Delta l} \ln\left(\frac{X_1(E_1)}{X_2(E_1)}\right) \quad (10)$$

$$= -\frac{1}{l_1 - l_2} \ln\left(\frac{X_1(E_1)}{X_2(E_1)}\right)$$

$$\beta(E_1, \text{Matériau}, \theta) = \frac{X_1(E_1)}{e^{-\mu'_{matériau}(E_0, E_1, \varepsilon) \cdot l_1}} \quad (11)$$

$$= \frac{X_1(E_1)}{e^{-l_1\left(-\frac{1}{(l_1 - l_2)} \ln \frac{X_1(E_1)}{X_2(E_1)}\right)}}$$

$$= \frac{X_1(E_1)}{e^{\left(-\frac{l_1}{(l_1 - l_2)} \ln \frac{X_1(E_1)}{X_2(E_1)}\right)}}$$

$$= \frac{X_1(E_1)}{\left(\frac{X_1(E_1)}{X_2(E_1)}\right)^{\frac{l_1}{(l_1 - l_2)}}}$$

$$= \frac{X_2(E_1)^{\frac{l_1}{(l_1 - l_2)}}}{X_1(E_1)^{\frac{l_1}{(l_1 - l_2)} - 1}}$$

$$= \frac{X_2(E_1)^{\frac{l_1}{(l_1 - l_2)}}}{X_1(E_1)^{\frac{l_2}{(l_1 - l_2)}}}$$

Figure 5:
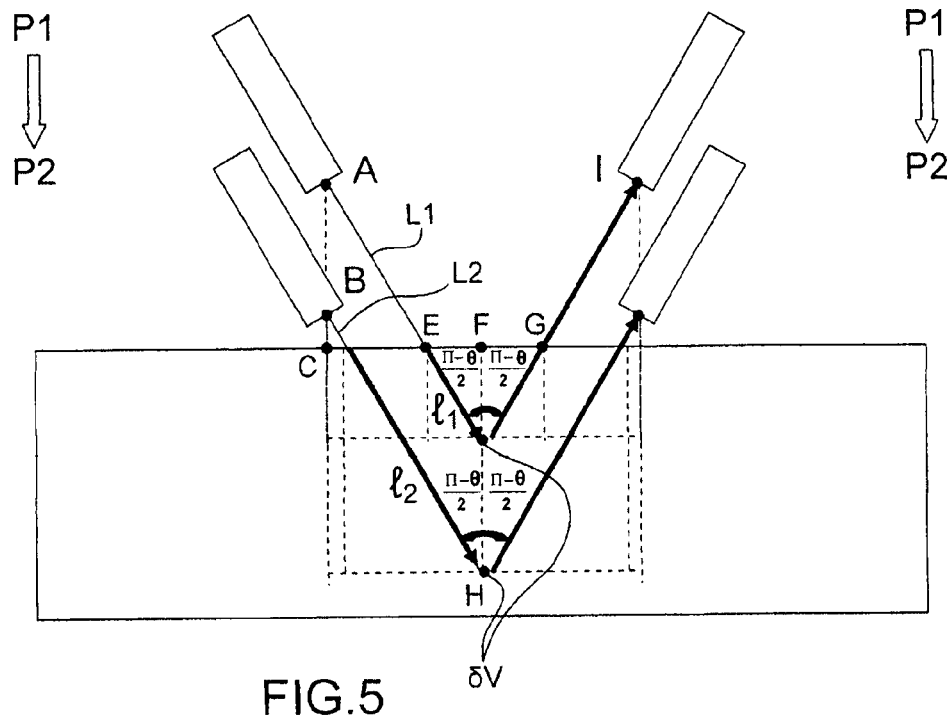
FIG. 5 represents in a geometric manner the multi-depth principle of the method according to the invention for the inspection of a mono material object.

For each of the measurement positions, the source of X-Ray photons 10—spectrometric detector 11 assembly is positioned with respect to the object 100, so as to know the scattering angle $\theta$ and to maintain it substantially constant. It is possible to determine geometrically $l_1$ and $l_2$ and consequently $\Delta l$, then the combined attenuation coefficient $\mu'_{material}(E_0, E_1, \epsilon)$ with the formulas (10) and (11) and optionally the parameter $\beta(E_1, \text{Material}, \theta)$. The two distances $l_1$ and $l_2$ may be expressed on the basis of the relative positions of the source of X-Ray photons 10, the spectrometric detector 11 and the object to be inspected 100. One uses the distance AI separating the source of X-Ray photons 10 from the spectrometric detector 11, the distances AC, BC separating the source of X-Ray photons 10 from the surface of the object 100 irradiated by the beam of incident X-Ray photons 12, in other words by which the beam of incident X-Ray photons 12 penetrates into the object 100, when the source of X-Ray photons 10-object 100 assembly is in the first position P1 and in the second position P2 respectively. The distances AI, AC, BC are illustrated in FIG. 5.

One notes:

$$\delta = \pi - \theta$$

$$l_1 = EF / \sin(\delta/2)$$

The point F is the projection of the inspection volume $\delta V$ not just at the first depth but at the second depth on the surface of the object 100 irradiated by the beam of incident X-Ray photons 12.

$$EF = AI/2 - CE = AI/2 - ACtg(\delta/2)$$

The point E is the point of the surface of the object 100 irradiated by the central axis of the beam of incident X-Ray photons 12 in the first measuring position P1.

$$l_1[AI/2 - ACtg(\delta/2)] / \sin(\delta/2) = \frac{AI}{2\sin(\delta/2)} - AC\frac{1}{\cos(\delta/2)}$$

The point D is the point of the surface of the object 100 irradiated by the central axis of the beam of incident X-Ray photons 12 in the second measuring position P2.

$$l_2 = DF / \sin(\delta/2)$$

$$DF = AI/2 - CD = AI/2 - BC\cot g(\delta/2)$$

$$l_2 = [AI/2 - BCtg(\delta/2)] / \sin(\delta/2) = \frac{AI}{2\sin(\delta/2)} - BC\frac{1}{\cos(\delta/2)}$$

Knowing $k(E_0, \theta)$ and knowing that it is independent of the material to be identified, the ratio $Z_{eff}\rho/A_{norm}$ may be deduced thereof such that:

$$\frac{Z_{eff} \cdot \rho}{A_{norm}} = \left[\frac{X_2(E_1)^{\frac{l_1}{(l_1 - l_2)}}}{X_1(E_1)^{\frac{l_2}{(l_1 - l_2)}}}\right] / k(E_0\theta) \quad (12)$$

$$= \beta(E_1, \text{Matériau}, \theta) / k(E_0\theta)$$

$k(E_0, \theta)$ will now be determined. It may be modelled, but advantageously it will be determined by measurement using a known standard material. The standard material being known, only $k(E_0, \theta)$ is unknown in the formula (3). It can thus be easily determined. With a known material and a source of X-Ray photons of which the flux of X-Ray photons of the beam of emitted X-Ray photons is known, by making two flux measurements of X-Ray photons of the beam of backscattered X-Ray photons in two different positions of the source of X-Ray photons spectrometric detector assembly, it is possible to determine:

$$X_{calib1}(E_1) = \beta(E_1, \text{Matériau} - \text{étalon}, \theta) \cdot e^{-\mu'_{matériau-étalon}(E_0, E_1, \varepsilon) \cdot l_1}$$

$$X_{calib2}(E_1) = \beta(E_1, \text{Matériau} - \text{étalon}, \theta) \cdot e^{-\mu'_{matériau-étalon}(E_0, E_1, \varepsilon) \cdot l_2}$$

-continued $$\beta(E_1, \text{Matériau} - \text{étalon}, \theta) = \frac{S(x,Z) \cdot \rho}{A_{norm}} k(E_0, \theta)$$

$$\approx \frac{Z_{eff} \cdot \rho}{A_{norm}} k(E_0, \theta)$$

The formulas presented above are valid for measurements in a vacuum or in air or, in a general manner, in a gas or a gaseous mixture or any other faintly absorbent medium at the energies $E_0$, $E_1$, in other words much less absorbent than the known material.

The explosive materials that interest us have sufficiently different densities p as illustrated in FIG. 3. It will now be explained how to estimate the density p of the material to be identified since in the method according to the invention one starts by estimating this density p.

Figure 6A:
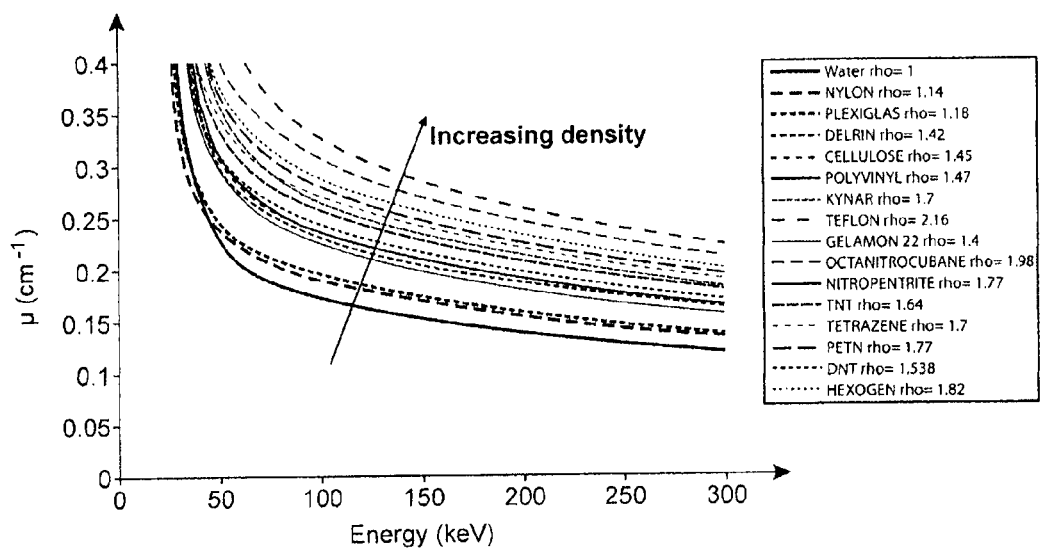
FIG. 6A is a representation of the linear attenuation coefficients of materials as a function of the energy of the X-Ray photons detected and FIG. 6B shows the relation between the density of the materials and the value of these linear attenuation coefficients for three energies, namely 50 keV, 100 keV and 150 keV.
Figure 6B:
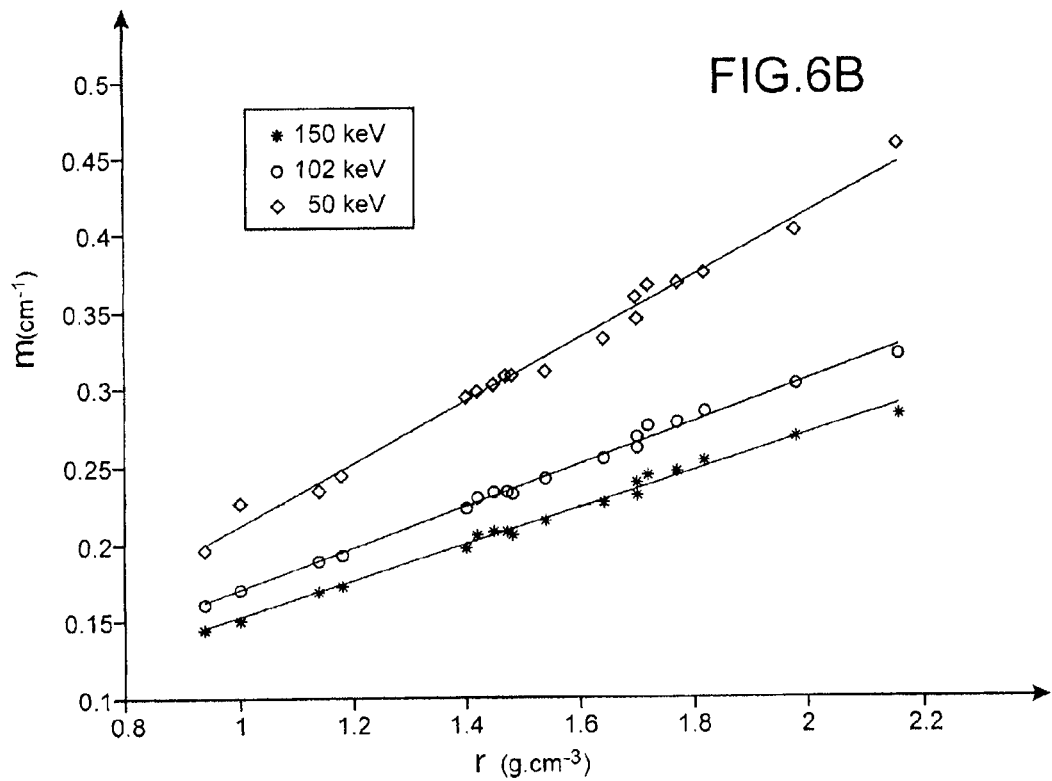

For sufficiently high energies, for example greater than around 30 keV, it will be noted in FIG. 6A, that the linear attenuation coefficients μ in the materials are ordered in the same sense as their densities ρ. Precisely, it will even be noted that the linear attenuation coefficient μ depends linearly on the density of the material as illustrated in FIG. 6B. The combined attenuation coefficient μ' is obtained from a linear combination of linear attenuation coefficients μ of the same material with two different energies $E_0$ and $E_1$.

$$\mu'_{mat\acute{e}riau}(E_0, E_1, \varepsilon) = \mu'_{mat\acute{e}riau}(E_0) \cdot \left[1 + \frac{\mu'_{mat\acute{e}riau}(E_1)}{\mu'_{mat\acute{e}riau}(E_0)} \cdot \varepsilon\right]$$

$$= \mu'_{mat\acute{e}riau}(E_0) + \mu'_{mat\acute{e}riau}(E_1) \cdot \varepsilon$$

Figure 7:
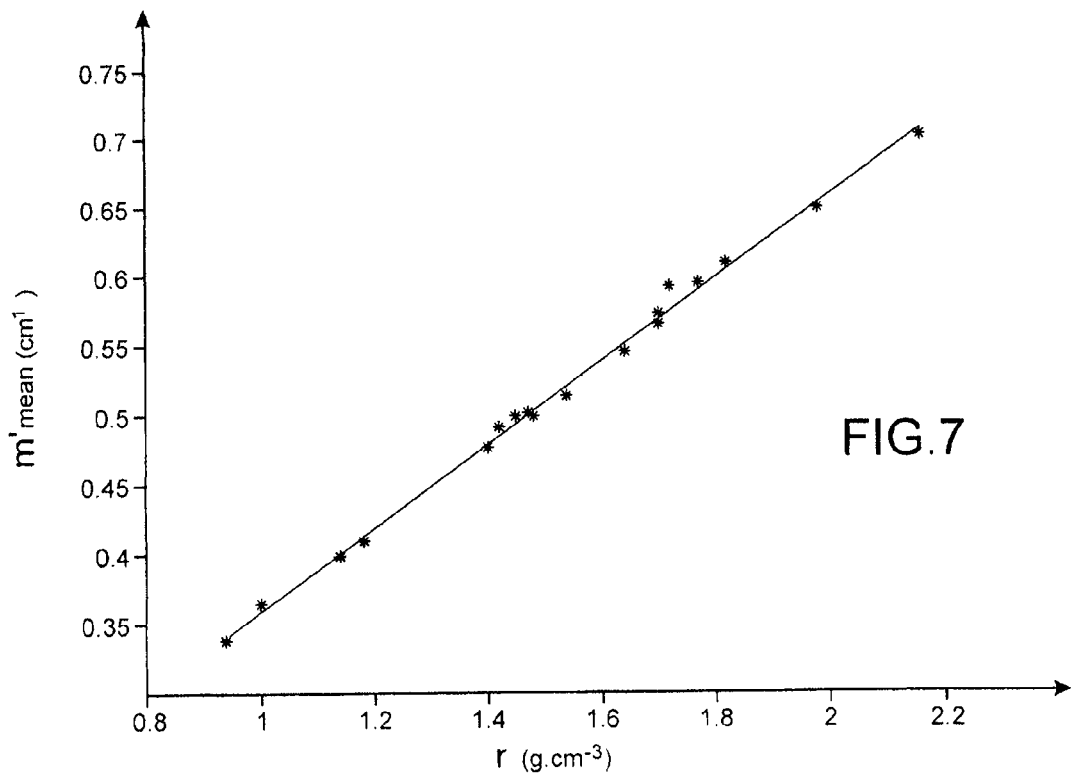
FIG. 7 is a representation of the mean value of the combined attenuation coefficient $\mu'_{material}(E_0,E_1,\epsilon)$ as a function of the density of these materials, this mean value having been calculated in a case where $\epsilon=1$, $\theta=120°$ and $E_1$ comprised in the range 50 keV to 100 keV.

It is deduced from this that a linear relation also exists between μ' and the density ρ of the material:

The densities of the materials represented in FIGS. 6A, 6B and 7 are given below.

| Material | Density ρ |
| --- | --- |
| Water | 1 |
| Nylon | 1.14 |
| Plexiglas | 1.18 |
| Delrin | 1.42 |
| Cellulose | 1.45 |
| Polyvinyl | 1.47 |
| Kynar | 1.7 |
| Teflon | 2.16 |
| Gelamon 22 | 1.4 |
| Octanitrocubane | 1.98 |
| Nitropentrite | 1.77 |
| TNT | 1.64 |
| Tetrazene | 1.7 |
| PETN | 1.77 |
| DNT | 1.538 |
| Hexogen | 1.82 |

FIG. 7 represents the correspondence between the density ρ of the materials and the mean of the combined attenuation coefficient $\mu'_{mean}$ for energies $E_1$ comprised between 50 and 100 keV in a specific experimental case in which $\varepsilon=1$ and $\theta=120°$.

This precise case confirms the strong relation of linearity between the arithmetic mean of the combined attenuation coefficient $\mu'_{mean}$ calculated by tables and the density ρ. In practice, the scattering angle θ and the ratio ε are known and depend on the geometry of the identifying device used, it is possible to estimate m (m whole number greater than one) combined attenuation coefficients $\mu'(E_0, E_1, \varepsilon)$ for a series of m values of energy $E_0$, such that the energy $E_1$, dependent on the energy $E_0$ and the scattering angle θ varies in a given range of energy, typically of several tens of keV, for example comprised between 50 keV and 100 keV. By realising the arithmetic mean of these m combined attenuation coefficients, the arithmetic mean of the combined attenuation coefficient $\mu'_{mean}$ is obtained, which depends on the known scattering angle θ and ratio ε.

It is possible to draw up a table of data obtained in an experimental manner for a given scattering angle θ and a ratio ε, this table making it possible to establish a relation of type:

$$\mu'_{mean}(\theta, \varepsilon) = a\rho + b.$$

It is thus possible to obtain an estimation of the density ρ of the material from this relation. The coefficients a and b can also be obtained by a calibration phase by making measurements with a given scattering angle θ and a ratio ε on a plurality of objects of known dimensions made of materials the density of which is known.

The relation linking the density ρ and the arithmetic mean of the combined attenuation coefficient $\mu'_{mean}$ is here linear but the calibration can show another type of relation, in general one thus has $\mu'_{mean} = f(\rho)$ A spectrometric detector will be used having a sufficiently high number of channels to cover all of the useful spectrometry signal, for example corresponding to a band of energy comprised between several keV and 200 keV. Channels corresponding to the lowest energies of the spectrum will be avoided, since the latter can be perturbed by noise at these energies and the linearity between the arithmetic mean of the combined attenuation coefficient $\mu'_{mean}$ and the density ρ is less precise.

It is then possible to estimate, from the formula (12), $Z_{eff}/A_{norm}$ as a function of $\beta(E_1,\text{Material},\theta)$ that will also have been calculated, $k(E_0)$ and ρ and represent $Z_{eff}/A_{norm}$ as a function of ρ as in FIG. 3, which makes it possible to identify the material.

Figure 8:
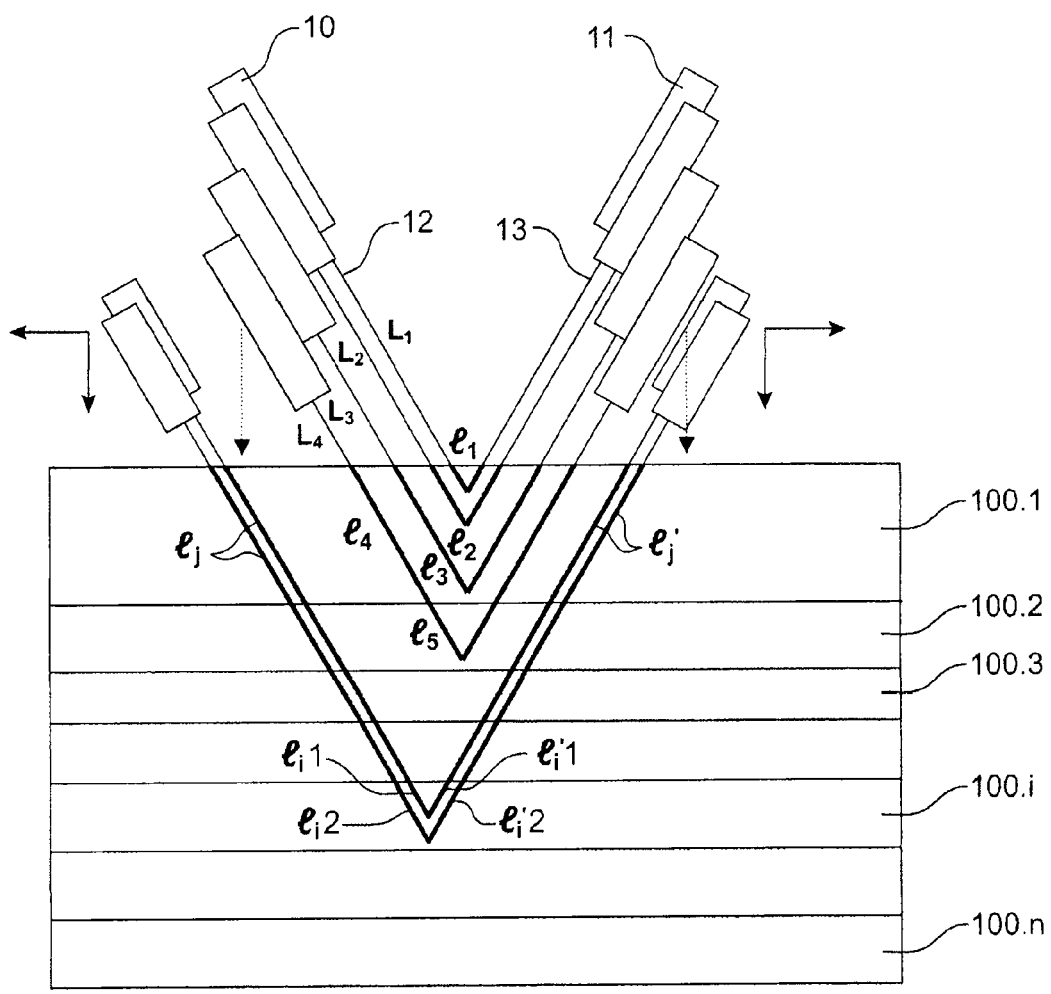
FIG. 8 illustrates the principle of the method of the invention for a multi material object with n layers.

It will now be explained, with reference to FIG. 8, how, according to the method of the invention, to identify in an object a material that is buried under one or more layers of other materials. It is assumed that each of the layers of the object is made of a homogeneous material, at least in the zone where the beam of incident X-Ray photons 12 and the beam of backscattered X-Ray photons 13 propagate. It is assumed that the object 100 is formed of n stacked layers referenced 100.1, 100.2, 100.3, ... 100.i, ... 100.n, n is a whole number greater than or equal to 1 The layers have an increasing rank the more one moves away from the surface that is irradiated by the beam of incident X-Ray photons 12. It is going to be necessary to make at least two measurements of the flux of X-Ray photons of the beam of backscattered X-Ray photons towards the spectrometric detector by layers, for two different scattering depths.

In the layer of rank i (i greater than or equal to 2) two fluxes are thus measured of X-Ray photons $X_{i1}(E_1)$ and $X_{i2}(E_1)$ of beams of backscattered X-Ray photons along a same backscattering angle θ from inspection volumes δV situated at different scattering depths. These fluxes of X-Ray photons are expressed in the following manner:

$$X_{i1}(E_1) = \beta(E_1, \text{Material}.i, \theta) \cdot e^{-\mu'_{material.i}(E_0, E_1, \varepsilon) \cdot li1} \cdot Fi \quad (13)$$

$$X_{i2}(E_1) = \beta(E_1, \text{Material}.i, \theta) \cdot e^{-\mu'_{material.i}(E_0, E_1, \varepsilon) \cdot li2} \cdot Fi \quad (14)$$

li1 and li2 are the distances traveled by the beam of incident X-Ray photons 12 in the material from the layer 100.i, up to the inspection volume.

The linear attenuation coefficient may be given by:

$$\mu'_{mat\acute{e}riau \cdot i}(E_0, E_1, \varepsilon) = -\frac{1}{li1 - li2} \ln\left(\frac{X_1(E_1)}{X_2(E_1)}\right)$$

li'1, li'2 designate the distances traveled by the beam of backscattered X-Ray photons in the layer 100.1 from the inspection volume. In a same layer 100.$i$ of material, the combined attenuation coefficient $\mu'_{material.i}(E_0,E_1,\varepsilon)$ remains constant. Here, the ratio $\varepsilon$ is such that $\varepsilon$=li'1/li1=li'2/li2.

The system of equations (13), (14) may be resolved to find the parameter $\beta(E_1,\text{Mat\'eriau}.i,\theta)$. The parameter is expressed by:

$$\beta(E_1, Mat\acute{e}riau \cdot i, \theta) = \frac{Xi2(E_1)^{\frac{li1}{(li1-li2)}}}{Xi1(E_1)^{\frac{li2}{(li1-li2)}}}$$

li1, li2, li'1, li'2 are calculated from the relative positions of the source of X-Ray photons, the spectrometric detector and the object, the distance lj traveled by the beam of incident X-Ray photons 12 in each of the one or more materials of rank 1 to i−1, the distance lj' traveled by the beam of backscattered X-Ray photons 13 in each of the one or more materials of rank 1 to i−1. To do this, successive flux measurements are made of X-Ray photons of backscattered beams for inspection volumes δV situated at greater and greater depths, from the surface layer and spaced apart by a step p, the scattering angle θ remaining substantially constant from one measurement to the next. Step p is chosen preferably small with respect to the thickness of the i−1 layers. For a successive first flux $X_1(E_1)$, a second flux $X_2(E_1)$ and a third flux $X_3(E_1)$ is calculated a first combined attenuation coefficient $$\mu'_1(E_0, E_1, \varepsilon) = -\frac{1}{lj1 - lj2} \ln\left(\frac{X_1(E_1)}{X_2(E_1)}\right)$$

and a second combined attenuation coefficient $$\mu'_2(E_0, E_1, \varepsilon) = -\frac{1}{lj2 - lj3} \ln\left(\frac{X_2(E_1)}{X_3(E_1)}\right),$$

with $\varepsilon$=lj'1/lj1=lj'2/lj2=lj'3/lj3, lj1, lj2, lj3 being the distances traveled by the beam of incident X-Ray photons 12 in the material in which is located the inspection volume for which the measurement is carried out, lj'1, lj'2, lj'3 being the distances travelled by the beam of backscattered X-Ray photons 13 in the material in which is located the inspection volume for which the measurement is carried out. These distances are calculated from the relative position between the source of X-Ray photons 10, the spectrometric detector 11 and the object 100, and step p. The first and the second combined attenuation coefficient are compared and as soon as a difference appears, one attributes to the searched for distance lj the greater of the distances used in the formula of the first combined attenuation coefficient. As soon as the first combined attenuation coefficient is very different from the second combined attenuation coefficient, it signifies that one has passed from one given layer to the next which is made of another material.

The distances lj, lj' make it possible to estimate the depth Pj of the boundary separating two different materials knowing the angle of incidence of the beam of incident X-Ray photons with respect to the surface of the material, said surface being considered as flat, at least locally, in other words between the zone of impact of the beam of incident X-Ray photons and the zone crossed by the beam of backscattered X-Ray photons along the angle θ.

Indeed, from the distance lj, it is possible to know the depth Pj of the interface between a layer of material of rank j and a layer of material of rank j+1 knowing the angle of incidence $\alpha_{inc}$ of the beam of incident X-Ray photons with respect to a normal N of the input face of the first layer 100.1 of the material analysed, according to the equality Pj=lj×sin($\alpha_{inc}$). The normal N is directed towards the exterior of the material.

Similarly, knowing lj', it is possible to estimate the depth Pj by knowing the angle $\alpha_{dif}$ of the beam of backscattered X-Ray photons with respect to the normal N cited beforehand according to the equality Pj=lj'×cos($\alpha_{dif}$).

It is assumed that the input surface of the first layer 100.1 of the analysed material is locally flat between the impact zone of the beam of incident X-Ray photons and the zone crossed by the beam of backscattered X-Ray photons along the angle θ. It will be noted moreover that $\theta=\alpha_{inc}+\alpha_{dif}$.

The calculation, calibration and attribution steps are reiterated one or more times by taking three successive fluxes of X-Ray photons, two successive ones thereof being fluxes used for the calculation of the preceding calculation step. The calculation of the distances traveled by the beam of X-Ray photons in the material in which is located the inspection volume for which the measurement is carried out takes into account the distance lj calculated previously.

One could also make the same reasoning by determining the coefficient $\beta(E_1,\text{material}.i,\varepsilon)$ with two of the successive measurements then with the two other successive measurements. A variation in the coefficient $\beta(E_1,\text{material}.i,\varepsilon)$ signals a change of material.

Knowing the angle of incidence of the beam of incident X-Ray photons with respect to the surface of the object observed, it is possible, knowing the distance lj traveled by the beam of incident X-Ray photons before backscattering in the layer j, to determine the depth of the boundary between the layer i and the layer j with respect to the surface of the object using simple trigonometric relations.

It is also necessary to determine the attenuation factor Fi, this attenuation depends on the materials of the i−1 layers 100.1 to 100.$i$ −1, crossed by the beam of incident X-Ray photons and the beam of backscattered X-Ray photons and covering the layer i.

$$Fi = \prod_{j=1}^{i-1} e^{-\mu'_{mat\acute{e}riau J}(E_0,E_1,\varepsilon) \cdot l_j} \tag{15}$$

with $\varepsilon$=lj'/lj lj corresponding to the distance traveled by the beam of incident X-Ray photons in the layer j and lj' corresponding to the distance traveled by the beam of backscattered X-Ray photons in the layer j.

For each of the i−1 layers, it is thus necessary to calculate the combined attenuation coefficient $\mu'_{material.j}(E_0,E_1,\varepsilon)$ thanks to two flux measurements $X_{j1}(E_1), X_{j2}(E_1)$ at different depths using the following formula:

$\mu'_{material.k}(E_0,E_1,\varepsilon)=(1/l1j-l2j)\ln(X_{j1}(E_1)/X_{j2}(E_1))$ $\epsilon = l1'j/l1j = l2'j/l2j$, $l1j$ and $l2j$ are the distances traveled by the beam of incident X-Ray photons in the material of the layer j up to the inspection volume corresponding to the measurement considered, $l1'j$ and $l2'j$ are the distances traveled by the beam of backscattered X-Ray photons in the material of the layer j up to the inspection volume corresponding to the considered measurement.

Figure 9:
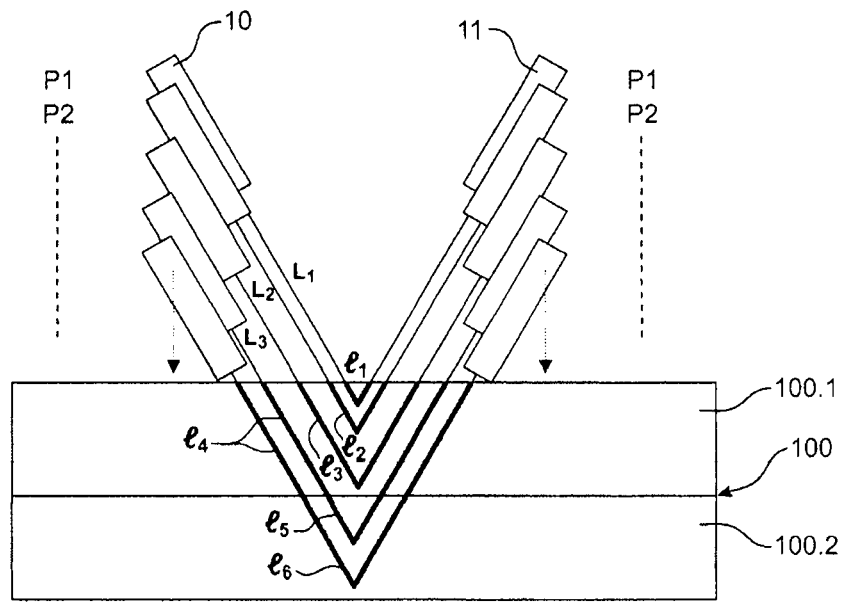
FIG. 9 illustrates the principle of the method of the invention for a multi material bilayer object.

Now that a general case has been described, the calculations for an object 100 having two stacked layers 100.1 and 100.2 will now be detailed, the first, superficial, made of a material.1, the second, buried, made of a material.2. Reference is made to FIG. 9. It is assumed that the object 100 only comprises two homogeneous stacked layers 100.1, 100.2.

Three flux measurements are made of X-Ray photons of beams of backscattered X-Ray photons, along the scattering angle θ, at three different depths in the superficial layer 100.1 and two in the buried layer 100.2.

These measurements are expressed in the following manner:

$$X_1(E_1) = \beta(E_1, \text{Matériau} \cdot 1, \theta) \cdot e^{-\mu'_{materiau1}(E_0,E_1,\epsilon) \cdot l_1}$$
$$X_2(E_1) = \beta(E_1, \text{Matériau} \cdot 1, \theta) \cdot e^{-\mu'_{materiau1}(E_0,E_1,\epsilon) \cdot l_2}$$
$$X_3(E_1) = \beta(E_1, \text{Matériau} \cdot 1, \theta) \cdot e^{-\mu'_{materiau1}(E_0,E_1,\epsilon) \cdot l_3}$$

(16)

$$X_4(E_1) = \beta(E_1, \text{Matériau} \cdot 2, \theta) \cdot e^{-\mu'_{materiau1}(E_0,E_1,\epsilon) \cdot l_4} e^{-\mu'_{materiau2}(E_0,E_1,\epsilon) \cdot l_5}$$
$$X_5(E_1) = \beta(E_1, \text{Matériau} \cdot 2, \theta) \cdot e^{-\mu'_{materiau1}(E_0,E_1,\epsilon) \cdot l_5} e^{-\mu'_{materiau2}(E_0,E_1,\epsilon) \cdot l_6}$$

(17)

The ratio ε again corresponds to the ratio of the distance traveled by the beam of backscattered X-Ray photons over the distance traveled by the beam of incident X-Ray photons in the material.

The combination of $X_1(E_1)$ and $X_2(E_1)$ makes it possible to calculate the parameter $\beta(E_1,\text{Matériau}.1,\theta)$ and the combined attenuation coefficient $\mu'_{material.1}(E_0,E_1,\epsilon)$ in the following manner:

$$\beta(E_1, \text{Matériau} \cdot 1, \theta) = \left( \frac{X_2(E_1)^{\frac{l_1}{(l_1-l_2)}}}{X_1(E_1)^{\frac{l_1}{(l_1-l_2)}}} \right)$$

$$\mu'_{materiau1}(E_0, E_1, \epsilon) = -\frac{1}{l_1-l_2}\left(\ln\left(\frac{X_1(E_1)}{X_2(E_1)}\right)\right)$$

By introducing the combined attenuation coefficient $\mu'_{material.1}(E_0,E_1,\epsilon)$ in the formulas of the fluxes (17), the combined attenuation coefficient $\mu'_{material.2}(E_0,E_1,\epsilon)$ and the parameter $\beta(E_1,\text{Matériau}.2,\theta)$ are obtained.

$$\Rightarrow \mu'_{materiau2}(E_0, E_1, \epsilon) = -\frac{1}{l_5-l_6}\left(\ln\left(\frac{X_4(E_1)}{X_5(E_1)}\right)\right)$$

$$\Rightarrow \beta(E_1, \text{Matériau} \cdot 2, \theta) = \frac{X_4(E_1)}{e^{-\mu'_{materiau1}(E_0,E_1,\epsilon) \cdot l_4} e^{-\mu'_{materiau2}(E_0,E_1,\epsilon) \cdot l_5}}$$

It only remains to estimate the density ρ with the mean of the combined attenuation coefficient r $\mu'_{mean}$. With the above magnitudes, it is possible to estimate the ratio Zeff/Anorm=$\beta E_1$, Material.2,θ)/k($E_0$,θ).ρ to be able to represent Zeff/Anorm as a function of ρ as in FIG. 3.

An example of identification of the material of an object by the method according to the invention will now be given. A cylindrical container 100.1 made of PETP ($C_{10}H_8O_4$) is used, the density ρ of which equals 1.32. The container 100.1 has a radius of 4 cm, a length of 32 cm and a thickness of 1 mm.

Figure 10:
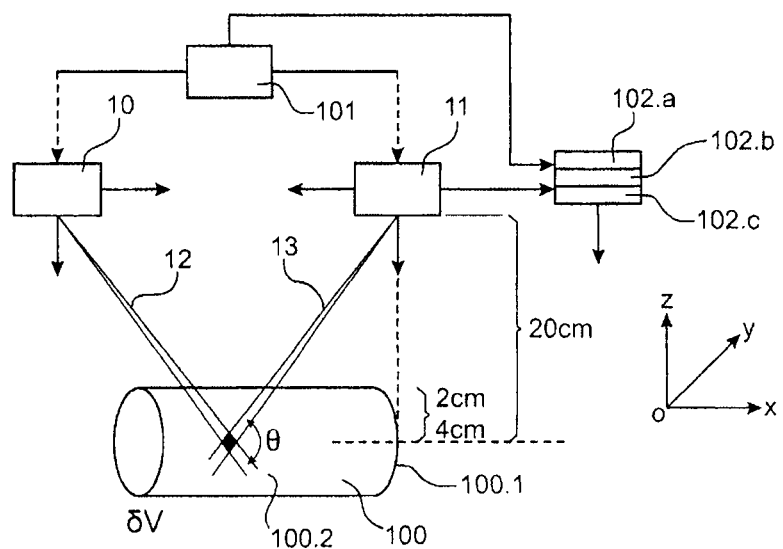
FIG. 10 illustrates the device for identifying a material of the invention used with a cylindrical object.

This container 100.1 is going to be filled with a material 100.2 that it is sought to identify by the method of the invention. Reference is made to FIG. 10. The referenced object 100 corresponds to the container 100.1 containing the material 100.2.

Two groups of materials are available. The first group of solid materials comprises: picric acid*, ammonal*, camphor*, cellulose, Delrin, DNT*, gum dynamite*, Gelamon 22*, Hexogen*, HMX ($C_4H_8N_8O_8$ or High Melting-Point Explosive)*, Kynar, ammonium nitrate*, nitropentrite*, nylon, nitroglycol*, octanitrocubane*, paraffin, pentrite or pentaeythritol tetranitrate or PETN*, PETP, Plexiglas, polyethylene, polystyrene, polyvinyl, black planting powder*, Teflon, Tetrazene*, TNT*.

The second group comprises five liquid materials such as water, hydrogen peroxide, nitroglycerine*, acetone, acetone peroxide. The materials followed by a "*" are explosives.

A source of X-Ray photons 10 of type XRS-3 was used supplying a beam of X-Ray photons of maximum energy of 270 kV, in pulses with 20 pulses per minute. The spectrometric detector 11 was a detector made of cadmium telluride.

The source of X-Ray photons 10 and the spectrometric detector 11 are placed in a plane xoy located at a distance of around 20 cm from the inspection volume δV. They are at the same distance from the surface of the object 100. This plane xoy is parallel to a generator of the cylinder forming the object 100. During one of the measurements of the flux of X-Ray photons of the beam of backscattered X-Ray photons by the spectrometric detector 11, the inspection volume δV is located at a depth of 2 cm in the container 100.1. During the other measurement, it is located at a depth of 4 cm. The inspection volume δV is located in the material 100.2. The scattering angle θ is equal to 120°. The spectrometric detector 11 and the source of X-Ray photons 10 are collimated, they have an opening of 2.4°. Means of adjusting 101 the relative position between the source of X-Ray photons 10, the spectrometric detector 11 and the object 100 are provided so as to place the inspection volume δV in at least two positions at different depths in the material 100.2 while maintaining the scattering angle substantially constant. The adjusting means 101 bring together and/or move apart the source of X-Ray photons-spectrometric detector assembly with respect to the object and bring together and/or move apart the source of X-Ray photons of the spectrometric detector. The movements, for example of the source of X-Ray photons 10-spectrometric detector 11 assembly take place along the direction z. It is also possible to move the source of photons 10 and/or the spectrometric detector along the direction x. The generator of the cylinder is directed along x. The adjusting means 101 make it possible to adjust the scattering angle θ on the one hand and the distance between the source of X-Ray-spectrometric detector assembly. The adjustment may take place step by step. The step may be constant or not. Advantageously, the step is chosen below the thickness of a layer of material of the object so that the inspection volume can take at least two positions in the layer of material. If it is sought to find the thickness of a layer of material, the step will be even smaller in order to make more than two flux measurements of X-Ray photons in a same layer.

Processing and calculation means 102.a are provided to process the fluxes of X-Ray photons measured by the spectrometric detector in the two positions and to calculate the combined attenuation coefficient $\mu'_{material}(E_0,E_1,\epsilon)$ by means of the fluxes of X-Ray photons measured in both positions.

The processing and calculation means 102.a can also calculate the parameter $\beta(E_1,Material,\theta)$ by means of the fluxes of X-Ray photons measured in the two positions.

Means are also provided for estimating 102.b the density ρ of the material from a mean $\mu'_{mean}$ of the combined attenuation coefficient $\mu'_{material}(E_0,E_1,\epsilon)$ over a given range of energy of the X-Ray photons of the beam of backscattered X-Ray photons. This mean $\mu'_{mean}$ is representative of the density ρ of the material.

There is also a means for determining 102.c the chemical nature of the material by means of the parameter $\beta(E_1,Material,\theta)$ describing the phenomenon of scattering, the combined attenuation coefficient $\mu'_{material}(E_0, E_1,\epsilon)$ and the density ρ.

These processing and calculation means 102.a receive the signals acquired by the spectrometric detector 11 and the geometric magnitudes linking the source of X-Ray photons 10 to the spectrometric detector 11 and to the object 100. Knowledge of μ', ρ, β enables the chemical nature of the examined material to be identified. The means of estimation 102.b and the means of determination 102.c receive the signals acquired by the spectrometric detector 11 and the geometric magnitudes linking the source of X-Ray photons 10 to the spectrometric detector 11 and to the object 100, as well as the signals delivered by the processing and calculating means 102.a.

The determination means 102.c may use the variation in the ratio $\beta(E_1,Material,\theta)/(k(E_0,\theta)\rho$ as a function of the density, and particularly to provide a graph representing $\beta(E_1,Material,\theta)/\rho.k(E_0,\theta)$ as a function of the density ρ as in FIG. 3 and/or the three functions μ', β, ρ.

Figure 11A:
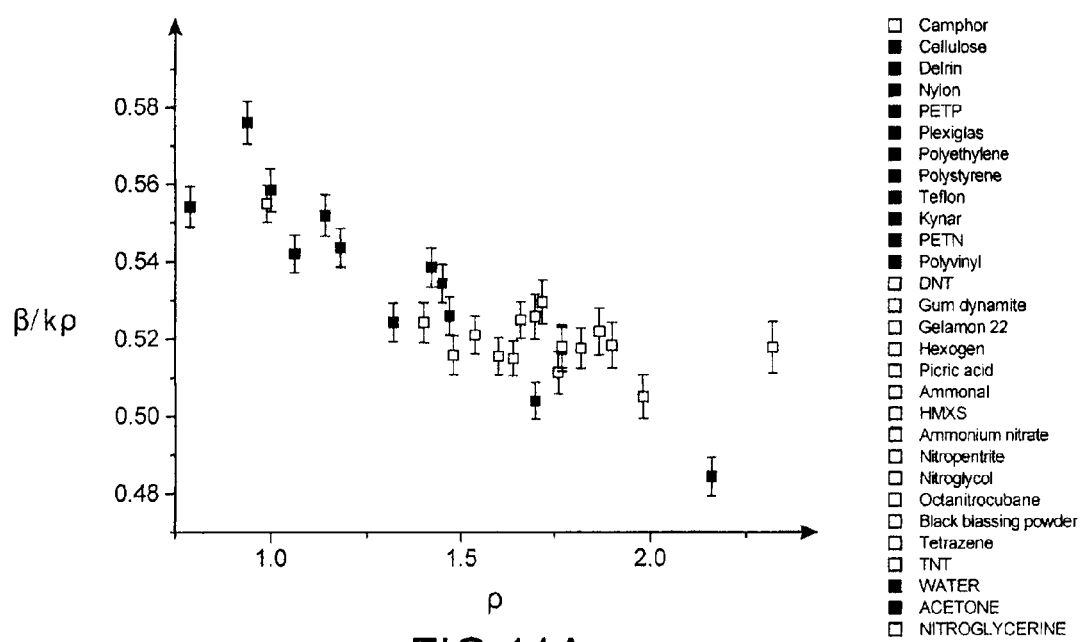
FIGS. 11A, 11C represent the ratio $\beta(E_1,\text{Material},\theta)/\rho.k(E_0,\theta)$ simulated as a function of the theoretical density $\rho$ for solid, respectively liquid, materials of interest contained in a container made of PETP which is a polyethyleneterephthalate.
Figure 11B:
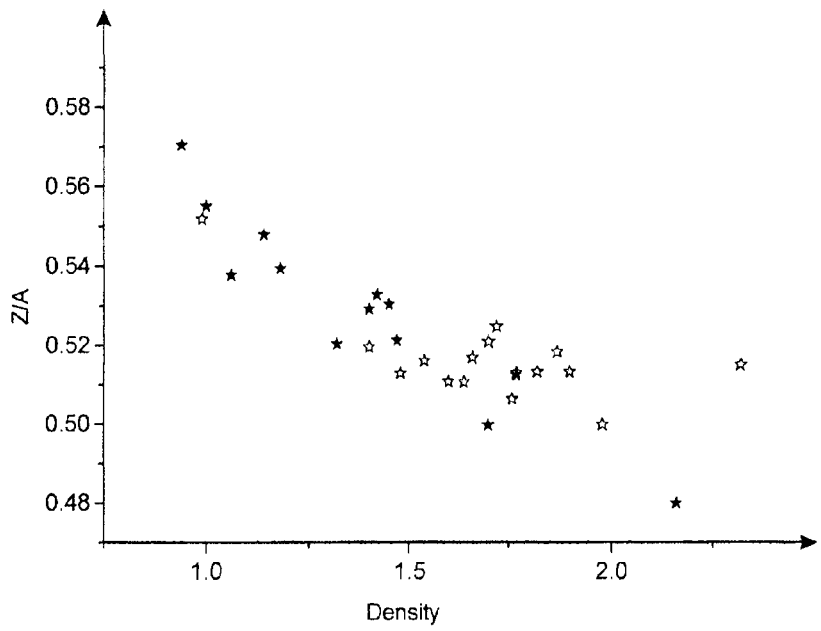
FIG. 11B represents the ratio of the theoretical effective atomic number over the molar mass as a function of the theoretical density.

The results of the calculations obtained by the method according to the invention are illustrated in FIG. 11A, which represents the variation in the ratio $\beta(E_1,Material,\theta)/\rho.k(E_0,\theta)$ as a function of the density ρ. In FIG. 11B is represented, for the same materials, the variation in the theoretical ratio $Z_{eff}/A_{norm}$ as a function of the density ρ. In these two representations, the density ρ is the theoretical density.

It may be noticed that the presence of the container has no influence on the determination of the material that it contains. The distribution of the values is substantially the same in FIG. 11A and in FIG. 11B.

In these FIGS. 11A, 11B, it is possible to distinguish clearly in the right-hand half of the graph an area of explosives. Several configurations have been employed for the position of the source of X-Ray photons—detector assembly with respect to the object. The best results in terms of precision have been obtained with the distance of 20 cm and the opening of 2.4° as indicated above. A greater spacing and a larger opening did not give such good results.

Figure 11C:
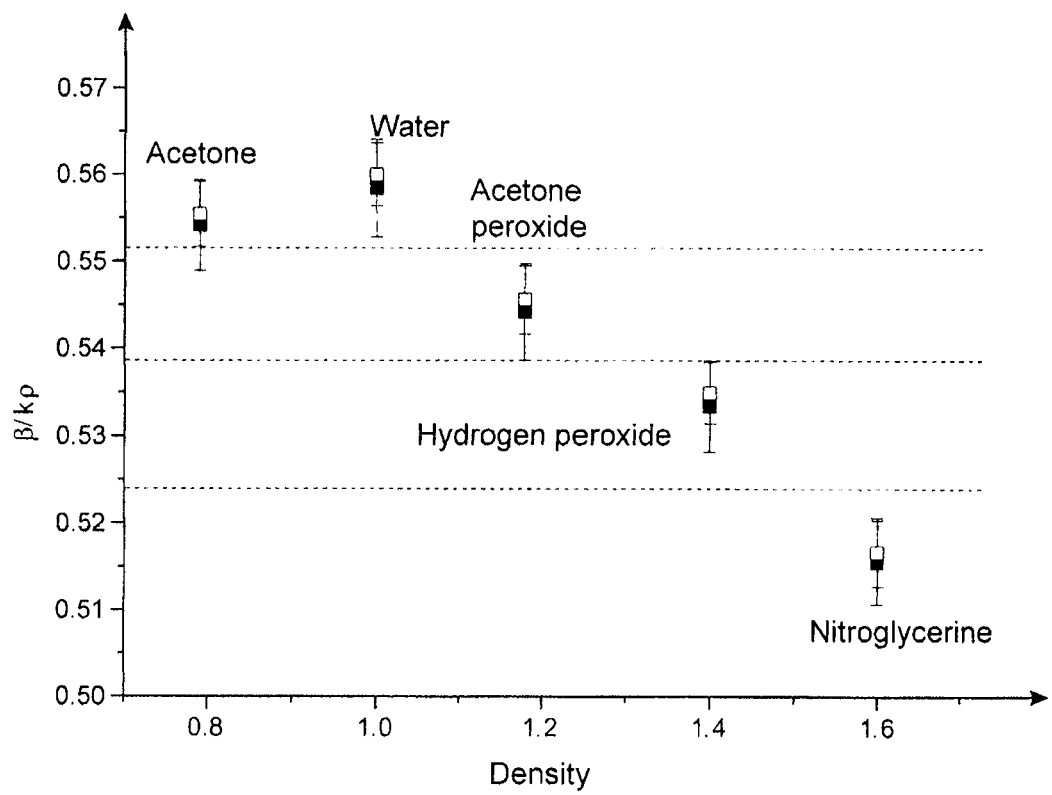

In FIG. 11C, for the five liquids of the second group, is represented the variation in the ratio $\beta(E_1,Material,\theta)/\rho.k(E_0,\theta)$ as a function of the density ρ from measurements of the relative magnitude to the radiation. Two series of measurements were carried out with different collimations for the source of X-Ray photons—spectrometric detector assembly. The opening of the source of X-Ray photons and that of the spectrometric detector were 1.2° and 1.5°, which makes the inspection volume pass from 0.65 cm³ to 1.43 cm³. The full points correspond to the opening of 1.2° and the empty points to the opening of 1.5°.

In FIGS. 11A, 11B, 11C, the values indicated are weighted means represented with error bars following a statistical study over 100 realisations. It will be noticed that liquids can be distinguished from solids, their density being lower.

In the same conditions of simulation as those described above and having led to the representations of FIGS. 11A and 11B, the estimated density μm has been calculated from the mean energy as has been explained from the expression (13).

Figure 12:
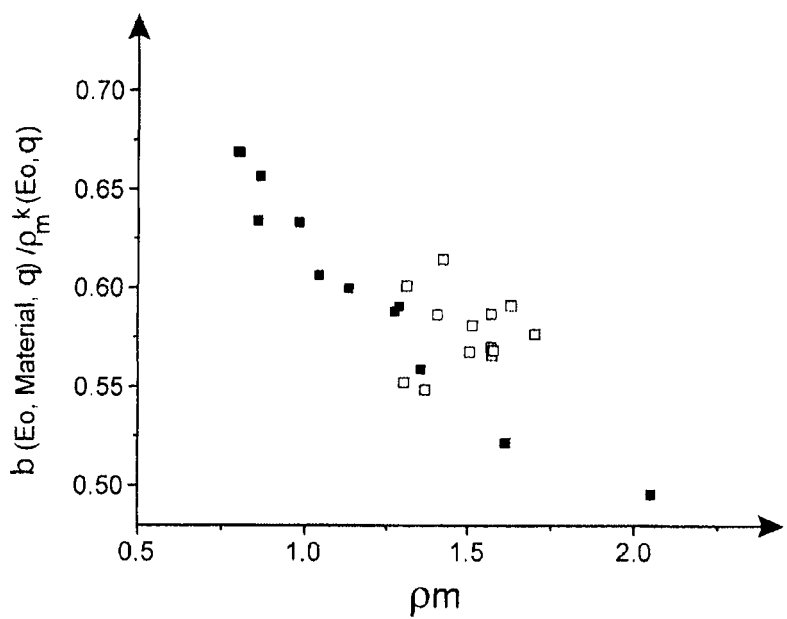
FIG. 12 illustrates, for the same solid materials as in FIG. 11A, the ratio $\beta(E_1,\text{Material},\theta)/\rho.k(E_0,\theta)$ as a function of $\rho$, $\beta(E_1,\text{Material},\theta)$ being calculated and $\rho$ estimated by the method of the invention.

In FIG. 12, the variation in the ratio $\beta(E_1,Material,\theta)/\mu m.k(E_0,\theta)$ has been represented as a function of μm for all of the materials tested in FIG. 11A and in the same geometric conditions. This representation is in good agreement with that of FIG. 11A.

The exploitation of the information provided by the beam of backscattered X-Ray photons while relying on the performances of the spectrometric detector is useful for in particular:

The identification of the nature of a liquid.

The distinction of water compared to an explosive liquid knowing that an explosive may be a mixture based on everyday products such as hydrogen peroxide, acetone, fertilizers, etc. or a liquid explosive such as nitroglycerine and acetone peroxide.

Although a certain embodiment of the present invention has been represented and described in a detailed manner, it will be understood that different changes and modifications may be made without going beyond the scope of the invention. It may in particular be envisaged that the object to be inspected is not overall in stacked layers, but that said stacking is only situated in an inspection area traveled by the beams of incident and backscattered X-Ray photons.

The device enabling the method described previously to be implemented may be a source of X-Ray photons, such as a collimated X-ray generator and a collimated spectrometric detector, both being moved between two consecutive measurements so that the collimation axis of the detector is centred on the same scattering angle θ with respect to the radiation produced by the source. The arrows in FIG. 8 illustrate the possible directions of movement.

According to another arrangement, the source of X-Ray photons is fixed, and the detector is moved in such a way that between two consecutive measurements the collimation axis is oriented along the same scattering angle θ with respect to the radiation produced by the source.

According to another arrangement illustrated in FIG. 4, the source of X-Ray photons 10 may be fixed, the detector 11 being formed of an arrangement of elementary collimated detectors 11.1, 11.2, ..., 11.n, the collimation axes being preferably parallel and oriented along a same scattering angle θ compared to the radiation produced by the source. It is then possible to compare at least two measurements of the backscattered radiation measured by at least two different detectors.

The invention claimed is:

1. A method for identifying a material of an object, the material being provided with a rank i (i whole number), i being equal to one if it is at the surface and being greater than one if it is buried under i−1 layers, the method comprising:
   a) a substantially flat surface, at least locally, of the object is irradiated with a beam of incident X-ray photons generated by a collimated source of X-ray photons;
   b) using a collimated spectrometric detector, a first flux of X-ray photons of a beam of backscattered X-ray photons is measured along a given scattering angle, generated after scattering of the beam of incident X-ray photons in a first inspection volume of the material of rank i, located at a first depth in the material of rank i;
   c) using the collimated spectrometric detector, a second flux of X-ray photons of a beam of backscattered X-ray photons is measured along the same given scattering angle, generated after scattering of the beam of incident X-ray photons in a second inspection volume of the material of rank i, located at a second depth in the material of rank i;
   d) using the measurements of the two fluxes of X-ray photons ($Xi1(E_1)$, $Xi2(E_1)$), a combined attenuation coefficient $\mu'_{material.i}(E_0,E_1,\epsilon)$ is calculated in which $E_0$ is the energy of the X-ray photons of the beam of incident X-ray photons and $E_1$ the energy of the X-ray photons of the beam of backscattered X-ray photons along the given scattering angle, comprising a natural logarithm of a ratio between the two fluxes ($Xi1(E_1)$, $Xi2(E_1)$),
   $\epsilon$ is a ratio such that $\epsilon=li'1/li1=li'2/li2$, $li1$ and $li2$ respectively being the distance traveled by the beam of incident X-ray photons in the material of rank i up to the first and second inspection volume, $li'1$ respectively and $li'2$ respectively being the distance traveled by the beam of backscattered X-ray photons in the material of rank i from the first and second inspection volume respectively;
   e) a mean of the combined attenuation coefficient $\mu'_{material.i}(E_0,E_1,\epsilon)$ is defined over a given energy range of the X-ray photons of the beam of backscattered X-ray photons;
   f) the density ρ of the material of rank i is estimated from the mean of the combined attenuation coefficient.

2. A method for identifying a material according to claim 1, in which the combined attenuation coefficient is expressed by:

$$\mu'_{material.i}(E_0, E_1, \varepsilon) = -\frac{1}{li1 - li2} \ln\left(\frac{Xi1(E_1)}{Xi2(E_1)}\right).$$

3. A method for identifying a material according to claim 1, in which a parameter $\beta(E_1,Material.i,\theta)$ is calculated describing the phenomenon of scattering in the material of rank i using measurements of the two fluxes of X-ray photons ($Xi1(E_1)$, $Xi2(E_i)$) which is expressed by:

$$\beta(E_1, Material.i, \theta) = \frac{Xi2(E_1)^{\frac{li1}{(li1-li2)}}}{Xi1(E_1)^{\frac{li2}{(li1-li2)}}}$$

and the variation in the ratio $\beta(E_1,Material.i,\theta)/(k(E_0,\theta)\rho$ is used as a function of the density to determine the chemical nature of the material of rank i, $k(E_0,\theta)$ being a parameter independent of the material of rank i but dependent on the energy of the beam of incident X-ray photons, the scattering angle, and the position of the source of X-ray photons and the spectrometric detector with respect to the inspected volume, the ratio being substantially equal to the ratio of the effective atomic number $Z_{eff}$ of the material over the normalized molar mass $A_{norm}$.

4. A method for identifying a material according to claim 1, in which the distances $li1$, $li2$, $li'1$, $li'2$ are calculated from relative positions of the source of X-ray photons, the spectrometric detector, and the object, and if i is different to 1, a distance $lj$ travelled by the beam of incident X-ray photons in each of the one or more materials of rank 1 to i−1 and a distance $l'j$ travelled by the beam of backscattered X-ray photons along the scattering angle in each of the one or more materials of rank 1 to i−1, while:
   1) making successive measurements of the flux of X-ray photons of the beam of backscattered X-ray photons for inspection volumes situated at greater and greater depths, from the surface layer and spaced apart by a step, the scattering angle remaining substantially constant from one measurement to the next;
   2) calculating for a first flux ($X_1(E_1)$), a second and a third flux of X-ray photons ($X_2(E_1)$, $X_3(E_1)$) of beams of backscattered X-ray photons a first combined attenuation coefficient $$\mu'_1(E_0, E_1, \varepsilon) = -\frac{1}{lj1 - lj2} \ln\left(\frac{Xj_1(E_1)}{Xj_2(E_1)}\right)$$

and a second combined attenuation coefficient $$\mu'_2(E_0, E_1, \varepsilon) = -\frac{1}{lj2 - lj3} \ln\left(\frac{Xj_2(E_1)}{Xj_3(E_1)}\right),$$

with $\epsilon=lj'1/lj1=lj'2/lj2=l'j3/lj3$, $lj1$, $lj2$, $lj3$ and respectively $l'j1$, $l'j2$, $l'j3$ being distances traveled by the beam of incident X-ray photons and respectively the beam of backscattered X-ray photons, in the material in which is located the inspection volume for which the measurement is made, these distances being calculated from the relative position between the source of X-Ray photons, the spectrometric detector, and the object;
   3) comparing the first and the second combined attenuation coefficients;
   4) as soon as a difference appears, the searched for distance $lj$ is the greater of the distances used in the formula of the first combined attenuation coefficient;
   5) reiterating operations 2) to 4) one or more times while taking three successive measurements of the flux of X-ray photons of the beam of backscattered X-ray photons, two of which are successive measurements used for the calculation of the preceding operation 2), the calculation of the distances travelled by the beam of incident and backscattered X-ray photons in the material in which is located the inspection volume for which the measurement is carried out, taking into account the distances $lj$ and $lj'$ determined previously.

5. Method for identifying a material according to claim 4, in which the factor Fi is expressed by $$Fi = \prod_{j=1}^{i-1} e^{-\mu'_{material,j}(E_0,E_1,\varepsilon)l_j},$$

with $\varepsilon=l_j'/l_j$ and $\mu'_{material,j}(E_0,E_1,\varepsilon)$ being a combined attenuation coefficient in the material of rank j, this combined attenuation coefficient being calculated from two measurements of the flux of X-ray photons of the beam of backscattered X-ray photons for two inspection volumes situated at two different depths in the material of rank j, the scattering angle remaining substantially constant during the two measurements, $l_j$ being the distance travelled by the beam of incident X-ray photons in the material of rank j and $l_j'$ the distance travelled by the beam of backscattered X-ray photons in the material of rank j.

6. A method for identifying a material according to claim 1, in which the parameter $k(E_0,\theta)$ is expressed by $$k(E_0, \theta) = C(E_0, \theta) \cdot F(E_0) \left[ \frac{d\sigma_{Kn}(E_0, \theta)}{d\Omega} \delta\omega N_a \cdot \delta V \right]$$

with $F(E_0)$ the flux density of the beam of incident X-ray photons, $N_a$ Avogadro's number, $$\frac{d\sigma_{KN}(E_0, \theta)}{d\Omega}$$

the differential cross section of scattering per electron by Compton effect approximated by a formula called Klein-Nishina, $\delta\omega$ the solid angle under which the spectrometric detector is seen from each point of the inspection volume $\delta V$, $C(E_0,\theta)$ the efficiency coefficient of the spectrometric detector at the energy $E_1$.

7. A method for identifying a material according to claim 1, in which the parameter $k(E_0, \theta)$ is obtained by modelling or by measurements in a standard material.

8. A device for identifying a material of an object comprising:
a collimated source of X-ray photons, a collimated spectrometric detector, the source of X-ray photons configured to irradiate a substantially flat surface, at least locally, of the object with a beam of incident X-ray photons, the spectrometric detector configured to measure a flux of X-ray photons of a beam of backscattered X-ray photons generated after scattering of the beam of Incident X-ray photons in an inspection volume of the material, the incident beam and the beam of backscattered X-ray photons forming a scattering angle, the vertex of which is the inspection volume;
an adjusting device configured to adjust the relative position between the source of X-ray photons, the spectrometric detector and the object so as to place the inspection volume in at least two positions at different depths in the material while maintaining the scattering angle substantially constant;
a processing device configured to process two fluxes of the beam of backscattered X-ray photons measured by the spectrometric detector in the at least two positions and to calculate a combined attenuation coefficient $\mu'_{material}(E_0,E_1,\varepsilon)$ by these two fluxes of X-ray photons; and
an estimating device configured to estimate the density of the material from the combined attenuation coefficient $\mu'_{material}(E_0,E_1,\varepsilon)$ averaged over a given range of energy of the X-ray photons of the beam of backscattered X-ray photons.

9. A device for identifying a material according to claim 8, in which the processing device makes it possible to calculate a parameter $\beta(E_1,\text{Material}, \theta)$ describing the phenomenon of scattering in the material of rank i.

10. A device for identifying a material according to claim 9, further comprising a determining device configured to determine the chemical nature of the material using the parameter $\beta(E_1,\text{Material},\theta)$, the combined attenuation coefficient $\mu'_{material}(E_0,E_1,\varepsilon)$ and the density, the determining device using the variation in the ratio $\beta(E_1,\text{Material},\theta)/(k(E_0,\theta)\rho$ as a function of the density, $k(E_0,\theta)$ being a parameter independent of the material but dependent on the energy of the beam of incident X-ray photons, the scattering angle, and the position of the source of X-ray photons and the spectrometric detector with respect to the inspected volume.

11. A device for identifying a material according to claim 8, in which the scattering angle is substantially constant for two successive measurements.

12. A device for identifying a material according to claim 8, in which the adjusting device brings together and/or moves apart the source of X-ray photons-spectrometric detector assembly with respect to the object, and brings together and/or moves apart the source of X-ray photons of the spectrometric detector.

13. A device for identifying a material according to claim 8, in which the means for adjusting device is configured to move step by step, while bringing together and/or moving apart the source of X-ray photons-spectrometric detector assembly with respect to the object, the step being smaller than the thickness of a layer of material of the object so that the inspection volume can take at least two positions in the layer of material.

* * * * *